United States Patent [19]

Robbins et al.

[11] Patent Number: 5,843,648
[45] Date of Patent: Dec. 1, 1998

[54] P15 AND TYROSINASE MELANOMA ANTIGENS AND THEIR USE IN DIAGNOSTIC AND THERAPEUTIC METHODS

[75] Inventors: Paul F. Robbins, Silver Spring; Steven A. Rosenberg, Potomac, both of Md.

[73] Assignee: The United States of America as represented by the Secretary, Department of Health and Human Services, Washington, D.C.

[21] Appl. No.: 370,909

[22] Filed: Jan. 10, 1995

[51] Int. Cl.[6] .............................. C12Q 1/68; C12P 19/34; C12N 15/70; C07H 21/02
[52] U.S. Cl. ......................... 435/6; 435/91.2; 435/172.3; 435/69.1; 435/320.1; 435/240.2; 435/252.3; 435/254.2; 435/7.1; 435/7.2; 435/7.9
[58] Field of Search ...................... 435/6, 91.2, 7.1–7.9, 435/172.3, 69.1, 320.1, 240.2, 252.3, 254.2; 536/23.1, 24.3, 24.33

[56] References Cited

U.S. PATENT DOCUMENTS 5,262,177 11/1993 Brown et al. .
5,342,774 8/1994 Boon et al. .

FOREIGN PATENT DOCUMENTS

| 0668350 | 8/1995 | European Pat. Off. . |
| 3341367 | 5/1984 | Germany . |
| 2133543 | 8/1984 | United Kingdom . |
| 9314189 | 7/1993 | WIPO . |
| 9414459 | 7/1994 | WIPO . |
| 9423067 | 10/1994 | WIPO . |
| 9522561 | 8/1995 | WIPO . |

OTHER PUBLICATIONS

Robbins, et al. (1994), "Recognition of tyrosinase by tumor–infiltrating lymphocates from a patient responding to immunotherapy", *Cancer Research;* 54:3124–3126.

Robbins, et al. (1995) "Cloning of a new gene encoding an antigen recognized by melanoma–specific HLA–A24–restricted tumor–infiltrating lymphocytes" *J. Immunol.* 1995; 154(11), 5944–50.

Coulie, P.G. et al. (1993) "Genes coding for tumor antigens recognized by human cytolytic T–lymphocytes." *J. Immunotherap.;* 14:104–109.

Coulie P.G. et al. "A new gene coding for a differentiation antigen recognized by autologous cytolytic T lymphocytes on HLA–A2 melanomas." *J. Exp. Med.* 1994; 180:35–42.

Maresh, C.A. et al.: "Cloning and expression of the gene for the melanoma associated ME20 antigen." *DNA and Cell Biology* 1994; 13:87–95.

Cox, A.L. et al. "Identification of a peptide recognized by five melanoma–specific human cytotoxic T cell lines." *Science* 1994; 264:716–719.

Brichard, V., et al.: "The tyrosinase gene codes for an antigen recognized by autologous cytolytic T lymphocytes on HLA–A2 melanomas". *J. Exp. Med.* 1993; 178:489–495.

Gaugler, B., et al. "Human gene MAGE–3 codes for an antigen recognized on a melanoma by autologous cytolytic T lymphocytes". *J. Exp. Med.* 1994; 179:921–930.

Traversari, C., et al.: "A nonapeptide encoded by human gene MAGE–1 is recognized on HLA–A1 by cytolytic T lymphocytes directed against tumor antigen MZ2–E". *J Exp. Med.* 1992; 176:1453–1457.

Cellis, E., et al.: "Induction of anti–tumor cytotoxic T lymphocytes in normal humans using primary cultures and synthetic peptides epitopes". *Proc. Natl. Acad. Sci. USA* 1994; 91:2105–2109.

Boon, T.: "Toward a genetic analysis of tumor rejection antigens". *Adv. Cancer Res.* 1992; 58:177–210.

Kawakami, Y., et al.: "T–cell recognition of human melanoma antigens." *J. Immunother.* 1993; 14:88–93.

Bakker, A.B.H., et al.: "Melanocyte lineage–specific antigen gp100 is recognized by melanocyte–derived tumor infiltrating lymphocytes." *J. Exp. Med.* 1994; 179:1005–1009.

Wölfel, T., et al.: "Two tyrosinase nonapeptides recognized on HLA–A2 melanomas by autologous cytolytic T. lymphocytes." *Eur. J. Immunol.* 1994; 24:759–764.

Adema, G.J., et al.: "Melanocyte lineage–specific antigens recognized by monoclonal antibodies NK1–beteb, HMB–50, and HMB–45 are encoded by a single cDNA." *Am J. Pathol.* 1993; 143:1579–1585.

Kwon, B.S., et al.: "A melanocyte–specific gene, Pmel 17, maps near the silver coat color locus on mouse chromosome 10 and is in a syntenic region on human chromosome 12." *Proc. Natl. Acad. Sci. USA* 1991; 88:9228–9232.

Rosenberg, S.A., et al.: "Use of tumor infiltrating lymphocytes and interleukin–2 in the immunotherapy of patients with metastatic melanoma. Preliminary report." *N. Engl. J. Med.* 1988; 319:1676–1680.

Kawakami, Y., et al.,: "Shared human melanoma antigens. Recognition by tumor infiltrating lymphocytes in HLA–A2.1 transfected melanomas." *J. Immunol* 1992; 148:638–643.

Van der Bruggen, et al.: "A gene encoding an antigen recognized by cytolytic T. lymphocytes on a human melanoma." *Science* 1991; 254:1643–1647.

(List continued on next page.)

*Primary Examiner*—W. Gary Jones
*Assistant Examiner*—Dianne Rees
*Attorney, Agent, or Firm*—Morgan & Finnegan, L.L.P.

[57] ABSTRACT

The present invention provides a nucleic acid sequence encoding a melanoma antigen recognized by T lymphocytes, designated p15. This invention further relates to bioassays using the nucleic acid sequence, protein or antibodies of this invention to diagnose, assess or prognoses a mammal afflicted with melanoma or metastata melanoma. This invention also provides immunogenic peptides derived from the p15 melanoma antigen and a second melanoma antigen designated tyrosinase. The proteins and peptides provided can serve as an immunogen or vaccine to prevent or treat melanoma.

14 Claims, 9 Drawing Sheets

OTHER PUBLICATIONS

Falk, K., et al.: "Allele–specific motifs revealed by sequencing of self–peptides eluted from MHC molecules." *Nature* 1991; 351:290–296.

Kubo, R., et al.: "Definition of specific peptide motifs for four major HLA–A Alleles." *Journal of Immunology* 1994, 152:3913–3924.

Parker, K., et al.: "Sequence motifs important for peptide binding to the human MHC class 1 molecule. HLA–A2." *J. Immunol.* 1992; 3580–3587.

Ruppert, J., et al.: "Prominent role of secondary anchor residues in peptide binding to HLA–A2.1 molecules." *Cell* 1993; 74:929–937.

Storkus, W., et al.: "Identification of human melanoma peptides recognized by class 1 restricted tumor infiltrating T lymphocytes." *Journal of Immunology* 1993; 151:3719–3727.

Kawakami, Y., et al.: "Cloning of the gene coding for a shared human melanoma antigen recognized by autologous T cells infiltrating into tumor." *Pro. Natl. Acad. Sci. USA* 1994; 91:3515–3519.

Adema, G.J. et al., "Molecular characterization of the melanocyte lineage–specific antigen gp100." *Journal of Biological Chemistry* 1994; 269:20126–20133.

EMBL Database Acession Number M32295: 26–11–90 Vogel A.: Human KD melanocyte specific secreted glycoprotein MRNA 3'end'.

Kawakami, Y., et al.: "Identification of a human melanoma antigen recognized by tumor–infiltrating lymphocytes associated with in vivo tumor rejection." *Proc. Natl. Acad. Sci. USA* 1994; 91:6458–6462.

Kawakami, Y., et al., "Identification of the Immunodominant Peptides of the MART–1 Human Melanoma Antigen Recognized by the Majority of HLA–A2–restricted Tumor Infiltrating Lymphocytes" *J. Exp. Med.* 180:347–352, 1994.

Rivoltini, L., et al., "Induction of Tumor–Reactive CTL from Peripheral Blood and Tumor–Infiltrating Lymphocytes of Melanoma Patients by In Vitro Stimulation with an Immunodominant Peptide of the Human Melanoma Antigen MART–1" *Journal of Immunology,* 1995, 154:2257–2265.

Slingluff, C.L.,Jr., et al., "Direct analysis of tumor–associated peptide antigens" *Current Opinion in Immunology* 1994, 6:733–740.

Cole, D.J., et al., "Characterization of the Functional Specificity of a Cloned T–Cell Receptor Heterodimer Recognizing the MART–1 Melanoma Antigen" *Cancer Res.* 55:748–752 Feb. 1995.

Cole, D.J., et al., "Identification of MART–1–specific T–Cell Receptors: T Cells Utilizing Distinct T–Cell Receptor Variable and Joining Regions Recognize the Same Tumor Epitope" *Cancer Res.* 54:5265–5268, 1994.

Castelli, C., et al., "Mass Spectrometric Identification of a Naturally Processed Melanoma Peptide Recognized by $CD8^+$ Cytotoxic T Lymphocytes" *J. Exp. Med.* 181:363–368 1995.

Sette, A., et al., "Peptide Binding To The Most Frequent HLA–A Class I Alleles Measured by Quantitative Molecular Binding Assays" *Molecular Immunology* 31:813–822, 1994.

Wölfel, T., et al., "Analysis Of Antigens Recognized On Human Melanoma Cells By A2–Restricted Cytolytic T Lymphocytes (CTL)" *Int. J. Cancer* 55:237–244, 1993.

Wölfel, T., et al., "Isolation of Naturally Processed Peptides Recognized by Cytolytic Lymphocytes (CTL) on Human Melanoma Cells in Association with HLA–A2.1" *Int. J. Cancer* 57:413–418, 1994.

Topalian, S.L., et al., "Human $CD4^+$ T Cells Specifically Recognize a Shared Melanoma–Associated Antigen Encoded by the Tyrosinase Gene" *PNAS* 91:9461–9465, 1994.

Boël, P., et al., "BAGE: a New Gene Encoding an Antigen Recognized on Human Melanomas by Cytolytic T Lymphocytes" *Immunology* 2:167–175 1995.

Slingluff, C.L., Jr., et al., "Recognition of Human Melanoma Cells by HLA–A2.1–Restricted Cytotoxic T Lymphocytes is Mediated by at Least Six Shared Peptide Epitopes" *Journal of Immunology* 150:2955–2963 1993.

Genbank Database Accession Number M77348—Human PMEL 17 in RNA–Nov. 14, 1991.

Genbank Database Accession Number U06654—Human Differentiation Antigen Melan–A Protein in RNA—Jul. 30, 1994.

Genbank Database Accession Number U06452—Human Melanoma Antigen Recognized by T–Cells (MAN7–1) MRNA—Jun. 25, 1994.

Genbank Database Accession Number S73003—GP100 Melanocyte Lineage Specific Antigen / PMELL 7—Jan. 25, 1995.

Genbank Database Accession Number U01874—Human ME20 MRNA May 27, 1994.

Bouchard, Brigitte, et al.: "Induction of pigmentation in mouse fibroblasts by expression of human tryosinance." *J. Exp. Med.* 1989; 169:2029–2042.

Tripathi, Ram K., et al.: "Tyrosinase Gene Mutations in Type I (Tyrosinase–Deficient) Oculocutaneous Albinism Define Two Clusts of Missense Substitutions." *American Journal of Medical Genetics* 1992; 43:865–871.

Oetting, William S. and King, Richard A.: "Molecular Basis of Type I (Tyrosinase–Related) Oculocutaneous Albinism: Mutations and Polymorphisms of the Human Tyrosinase Gene." *Human Mutation* 1993; 2:1–6.

Spritz, Richard A.: "Molecular Genetics of Oculocutaneous Albinism." *Seminars in Dermatology* 1993; vol. 12, No.3:167–172.

FIG. 1

```
         10         20         30         40         50         60
AGCGGCGAGG GCTGGATCCT GGGCCAAATA TATGCCAACA ACGACAAGCT CTCCAAGAGG 70         80         90        100        110        120
CTGAAGAAAG TGTGGAAGCC ACAGCTGTTT GAGCGAGAGT TCTACAGTGA GATCCTGGAC 130        140        150        160        170        180
AAGAAGTTCA CAGTGACTGT GACCATGCGG ACCCTGGACC TCATCGATGA GGCTTACGGG
                              M   R   T   L   D   L   I   D   E   A   Y   G 190        200        210        220        230        240
CTCGACTTTT ACATCCTCAA GACCCCGAAG GAGGACCTGT GCTCCAAGTT TGGGATGGAG
 L   D   F   Y   I   L   K   T   P   K   E   D   L   C   S   K   F   G   M   E 250        260        270        280        290        300
CTGAAGCGAG GGATGCTGCT GCGGCTTGCC CGGCAGGACC CCCAGCTGCA CCCCGAGGAC
 L   K   R   G   M   L   L   R   L   A   R   Q   D   P   Q   L   H   P   E   D 310        320        330        340        350        360
CCCGAGCGGC GGGCAGCCAT CTACGACAAG TACAAGGAAT TTGCCATCCC AGAGGAGGAG
 P   E   R   R   A   A   I   Y   D   K   Y   K   E   F   A   I   P   E   E   E 370        380        390        400        410        420
GCAGAGTGGG TGGGCCTCAC GCTGGAGGAG GCCATTGAGA AGCAGAGACT TTTGGAGGAG
 A   E   W   V   G   L   T   L   E   E   A   I   E   K   Q   R   L   L   E   E 430        440        450        460        470        480
AAGGACCCTG TACCCCTGTT CAAGATCTAT GTGGCGGAGC TGATCCAGCA GCTGCAGCAG
 K   D   P   V   P   L   F   K   I   Y   V   A   E   L   I   Q   Q   L   Q   Q 490        500        510        520        530        540
CAGGCACTGT CAGAGCCGGC GGTGGTGCAG AAGACAGCCA GTGGCCAGTG ACCACACAGC
 Q   A   L   S   E   P   A   V   V   Q   K   T   A   S   G   Q 550        560        570        580        590        600
TCCTCCATGC CTGACCAACA GGCCCAGCTT TCCCTGCCAG GCCCTTTGCA CTGAGGACAC 610        620        630        640        650        660
AGATCCCGGG GAGCTGTGAG GGCCACCGGT GGGCAGTGGG TGGATCCTGG TTTCGTGTGC 670        680        690        700        710        720
TGCCCATGCA CCTTCCAGCC CGGGGCCAGC TTGGCAGGGA TCCCCAGGAG GCCTGGGCCG 730        740        750        760        770        780
CCCAGAGGCT CCTCTCAGGC TGGGCCCCGA CGTTTGCGGC AGTGTTCCTT GTCCCGTGGG 790        800
GCCGGGAGCG AGTAAAGTCT GGGCCAGGC
```

FIG. 3

```
              10         20         30         40         50
p15    ATGCGGACCC TGGACCTCAT CGATGAGGCT TACGGGCTCG ACTTTTACAT
         M  R  T   L  D  L  I   D  E  A   Y  G  L   D  F  Y  I

Clone 1   ..........  ..........  ..........  ..........  ..........
           .  .  .    .  .  .  .   .  .  .    .  .  .  .   .  .  .  .

Clone 2   ..........  ..........  .A........  ..........  ..........
           .  .  .    .  .  .  .   N  .  .    .  .  .  .   .  .  .  .

60         70         80         90        100
p15    CCTCAAGACC CCGAAGGAGG ACCTGTGCTC CAAGTTTGGG ATGGAGCTGA
         L  K  T   P  K  E   D  L  C  S   K  F  G   M  E  L

Clone 1   ..........  ..........  ..........  ..........  ..........
           .  .  .    .  .  .  .   .  .  .  .   .  .  .    .  .  .  .

Clone 2   .....G.CTG GGCCCC..C. TTTGCG...AG TGTTCC.T.T CCC.T.GG.C
           .  R  L   G  P  D   V  C  G  S   V  P  C   P  V  G
```

FIG. 7A

Sequence Range: 1 to 1910

```
         10         20         30         40         50         60
TGCAGACCTT GTGAGGACTA GAGGAAGAAT GCTCCTGGCT GTTTTGTACT GCCTGCTGTG
ACGTCTGGAA CACTCCTGAT CTCCTTCTTA CGAGGACCGA CAAAACATGA CGGACGACAC
                                         M    L  L  A  V  L  Y    C  L  L  W>

70         80         90        100        110        120
GAGTTTCCAG ACCTCCGCTG GCCATTTCCC TAGTGCCTGT GTCTCCTCTA AGAACCTGAT
CTCAAAGGTC TGGAGGCGAC CGGTAAAGGG ATCACGGACA CAGAGGAGAT TCTTGGACTA
  S  F  Q    T  S  A    G  H  F  P    S  A  C    V  S  S    K  N  L  M>

130        140        150        160        170        180
GGAGAAGGAA TGCTGTCCAC CGTGGAGCGG GGACAGGAGT CCCTGTGGCC AGCTTTCAGG
CCTCTTCCTT ACGACAGGTG GCACCTCGCC CCTGTCCTCA GGGACACCGG TCGAAAGTCC
  E  K  E    C  C  P    P  W  S    G  D  R  S    P  C  G    Q  L  S  G>

190        200        210        220        230        240
CAGAGGTTCC TGTCAGAATA TCCTTCTGTC CAATGCACCA CTTGGGCCTC AATTTCCCTT
GTCTCCAAGG ACAGTCTTAT AGGAAGACAG GTTACGTGGT GAACCCGGAG TTAAAGGGAA
  R  G  S    C  Q  N    I  L  L  S    N  A  P    L  G  P    Q  F  P  F>

250        260        270        280        290        300
CACAGGGGTG GATGACCGGG AGTCGTGGCC TTCCGTCTTT TATAATAGGA CCTGCCAGTG
GTGTCCCCAC CTACTGGCCC TCAGCACCGG AAGGCAGAAA ATATTATCCT GGACGGTCAC
  T  G  V    D  D  R    E  S  W    P  S  V  F    Y  N  R    T  C  Q  C>

310        320        330        340        350        360
CTCTGGCAAC TTCATGGGAT TCAACTGTGG AAACTGCAAG TTTGGCTTTT GGGGACCAAA
GAGACCGTTG AAGTACCCTA AGTTGACACC TTTGACGTTC AAACCGAAAA CCCCTGGTTT
  S  G  N    F  M  G    F  N  C  G    N  C  K    F  G  F    W  G  P  N>

370        380        390        400        410        420
CTGCACAGAG AGACGACTCT TGGTGAGAAG AAACATCTTC GATTTGAGTG CCCCAGAGAA
GACGTGTCTC TCTGCTGAGA ACCACTCTTC TTTGTAGAAG CTAAACTCAC GGGGTCTCTT
  C  T  E    R  R  L    L  V  R  R    N  I  F    D  L  S    A  P  E  K>

430        440        450        460        470        480
GGACAAATTT TTTGCCTACC TCACTTTAGC AAAGCATACC ATCAGCTCAG ACTATGTCAT
CCTGTTTAAA AAACGGATGG AGTGAAATCG TTTCGTATGG TAGTCGAGTC TGATACAGTA
  D  K  F    F  A  Y    L  T  L  A    K  H  T    I  S  S    D  Y  V  I>

490        500        510        520        530        540
CCCCATAGGG ACCTATGGCC AAATGAAAAA TGGATCAACA CCCATGTTTA ACGACATCAA
GGGGTATCCC TGGATACCGG TTTACTTTTT ACCTAGTTGT GGGTACAAAT TGCTGTAGTT
  P  I  G    T  Y  G    Q  M  K  N    G  S  T    P  M  F    N  D  I  N>

550        560        570        580        590        600
TATTTATGAC CTCTTTGTCT GGATGCATTA TTATGTGTCA ATGGATGCAC TGCTTGGGGG
ATAAATACTG GAGAAACAGA CCTACGTAAT AATACACAGT TACCTACGTG ACGAACCCCC
  I  Y  D    L  F  V    W  M  H  Y    Y  V  S    M  D  A    L  L  G  G>

610        620        630        640        650        660
ATCTGAAATC TGGAGAGACA TTGATTTTGC CCATGAAGCA CCAGCTTTTC TGCCTTGGCA
TAGACTTTAG ACCTCTCTGT AACTAAAACG GGTACTTCGT GGTCGAAAAG ACGGAACCGT
  S  E  I    W  R  D    I  D  F  A    H  E  A    P  A  F    L  P  W  H>
```

FIG. 7B

```
            670        680        690        700        710        720
     TAGACTCTTC TTGTTGCGGT GGGAACAAGA AATCCAGAAG CTGACAGGAG ATGAAAACTT
     ATCTGAGAAG AACAACGCCA CCCTTGTTCT TTAGGTCTTC GACTGTCCTC TACTTTTGAA
       R  L  F   L  L  R   W  E  Q  E   I  Q  K   L  T  G   D  E  N  F>

730        740        750        760        770        780
     CACTATTCCA TATTGGGACT GGCGGGATGC AGAAAAGTGT GACATTTGC A CAGATGAGTA
     GTGATAAGGT ATAACCCTGA CCGCCCTACG TCTTTTCACA CTGTAAACGT GTCTACTCAT
       T  I  P   Y  W  D   W  R  D  A   E  K  C   D  I  C   T  D  E  Y>

790        800        810        820        830        840
     CATGGGAGGT CAGCACCCCA CAAATCCTAA CTTACTCAGC CCAGCATCAT TCTTCTCCTC
     GTACCCTCCA GTCGTGGGGT GTTTAGGATT GAATGAGTCG GGTCGTAGTA AGAAGAGGAG
       M  G  G   Q  H  P   T  N  P  N   L  L  S   P  A  S   F  F  S  S>

850        860        870        880        890        900
     TTGGCAGATT GTCTGTAGCC GATTGGAGGA GTACAACAGC CATCAGTCTT TATGCAATGG
     AACCGTCTAA CAGACATCGG CTAACCTCCT CATGTTGTCG GTAGTCAGAA ATACGTTACC
       W  Q  I   V  C  S   R  L  E  E   Y  N  S   H  Q  S   L  C  N  G>

910        920        930        940        950        960
     AACGCCCGAG GGACCTTTAC GGCGTAATCC TGGAAACCAT GACAAATCCA GAACCCCAAG
     TTGCGGGCTC CCTGGAAATG CCGCATTAGG ACCTTTGGTA CTGTTTAGGT CTTGGGGTTC
       T  P  E   G  P  L   R  R  N  P   G  N  H   D  K  S   R  T  P  R>

970        980        990       1000       1010       1020
     GCTCCCCTCT TCAGCTGATG TAGAATTTTG CCTGAGTTTG ACCCAATATG AATCTGGTTC
     CGAGGGGAGA AGTCGACTAC ATCTTAAAAC GGACTCAAAC TGGGTTATAC TTAGACCAAG
       L  P  S   S  A  D   V  E  F  C   L  S  L   T  Q  Y   E  S  G  S>

1030       1040       1050       1060       1070       1080
     CATGGATAAA GCTGCCAATT TCAGCTTTAG AAATACACTG GAAGGATTTG CTAGTCCACT
     GTACCTATTT CGACGGTTAA AGTCGAAATC TTTATGTGAC CTTCCTAAAC GATCAGGTGA
       M  D  K   A  A  N   F  S  F  R   N  T  L   E  G  F   A  S  P  L>

1090       1100       1110       1120       1130       1140
     TACTGGGATA GCGGATGCCT CTCAAAGCAG CATGCACAAT GCCTTGCACA TCTATATGAA
     ATGACCCTAT CGCCTACGGA GAGTTTCGTC GTACGTGTTA CGGAACGTGT AGATATACTT
       T  G  I   A  D  A   S  Q  S  S   M  H  N   A  L  H   I  Y  M  N>

1150       1160       1170       1180       1190       1200
     TGGAACAATG TCCCAGGTAC AGGGATCTGC CAACGATCCT ATCTTCCTTC TTCACCATGC
     ACCTTGTTAC AGGGTCCATG TCCCTAGACG GTTGCTAGGA TAGAAGGAAG AAGTGGTACG
       G  T  M   S  Q  V   Q  G  S  A   N  D  P   I  F  L   L  H  H  A>

1210       1220       1230       1240       1250       1260
     ATTTGTTGAC AGTATTTTTG AGCAGTGGCT CCGAAGGCAC CGTCCTCTTC AAGAAGTTTA
     TAAACAACTG TCATAAAAAC TCGTCACCGA GGCTTCCGTG GCAGGAGAAG TTCTTCAAAT
       F  V  D   S  I  F   E  Q  W  L   R  R  H   R  P  L   Q  E  V  Y>

1270       1280       1290       1300       1310       1320
     TCCAGAAGCC AATGCACCCA TTGGACATAA CCGGGAATCC TACATGGTTC CTTTTATACC
     AGGTCTTCGG TTACGTGGGT AACCTGTATT GGCCCTTAGG ATGTACCAAG GAAAATATGG
       P  E  A   N  A  P   I  G  H  N   R  E  S   Y  M  V   P  F  I  P>
```

FIG. 7C

```
        1330       1340       1350       1360       1370       1380
    ACTGTACAGA AATGGTGATT TCTTTATTTC ATCCAAAGAT CTGGGCTATG ACTATAGCTA
    TGACATGTCT TTACCACTAA AGAAATAAAG TAGGTTTCTA GACCCGATAC TGATATCGAT
      L  Y  R   N  G  D   F  F  I  S   S  K  D   L  G  Y   D  Y  S  Y>

1390       1400       1410       1420       1430       1440
    TCTACAAGAT TCAGACCCAG ACTCTTTTCA AGACTACATT AAGTCCTATT TGGAACAAGC
    AGATGTTCTA AGTCTGGGTC TGAGAAAAGT TCTGATGTAA TTCAGGATAA ACCTTGTTCG
      L  Q  D   S  D  P   D  S  F   Q  D  Y  I   K  S  Y   L  E  Q  A>

1450       1460       1470       1480       1490       1500
    GAGTCGGATC TGGTCATGGC TCCTTGGGGC GGCGATGGTA GGGGCCGTCC TCACTGCCCT
    CTCAGCCTAG ACCAGTACCG AGGAACCCCG CCGCTACCAT CCCCGGCAGG AGTGACGGGA
      S  R  I   W  S  W   L  L  G  A   A  M  V   G  A  V   L  T  A  L>

1510       1520       1530       1540       1550       1560
    GCTGGCAGGG CTTGTGAGCT TGCTGTGTCG TCACAAGAGA AAGCAGCTTC CTGAAGAAAA
    CGACCGTCCC GAACACTCGA ACGACACAGC AGTGTTCTCT TTCGTCGAAG GACTTCTTTT
      L  A  G   L  V  S   L  L  C   R  H  K  R   K  Q  L   P  E  E  K>

1570       1580       1590       1600       1610       1620
    GCAGCCACTC CTCATGGAGA AAGAGGATTA CCACAGCTTG TATCAGAGCC ATTTATAAAA
    CGTCGGTGAG GAGTACCTCT TTCTCCTAAT GGTGTCGAAC ATAGTCTCGG TAAATATTTT
      Q  P  L   L  M  E   K  E  D  Y   H  S  L   Y  Q  S   H  L>

1630       1640       1650       1660       1670       1680
    GGCTTAGGCA ATAGAGTAGG GCCAAAAAGC CTGACCTCAC TCTAACTCAA AGTAATGTCC
    CCGAATCCGT TATCTCATCC CGGTTTTTCG GACTGGAGTG AGATTGAGTT TCATTACAGG 1690       1700       1710       1720       1730       1740
    AGGTTCCCAG AGAATATCTG CTGGTATTTT TCTGTAAAGA CCATTTGCAA AATTGTAACC
    TCCAAGGGTC TCTTATAGAC GACCATAAAA AGACATTTCT GGTAAACGTT TTAACATTGG 1750       1760       1770       1780       1790       1800
    TAATACAAAG TGTAGCCTTC TTCCAACTCA GGTAGAACAC ACCTGTCTTT GTCTTGCTGT
    ATTATGTTTC ACATCGGAAG AAGGTTGAGT CCATCTTGTG TGGACAGAAA CAGAACGACA 1810       1820       1830       1840       1850       1860
    TTTCACTCAG CCCTTTTAAC ATTTTCCCCT AAGCCCATAT GTCTAAGGAA AGGATGCTAT
    AAAGTGAGTC GGGAAAATTG TAAAAGGGGA TTCGGGTATA CAGATTCCTT TCCTACGATA 1870       1880       1890       1900       1910
    TTGGTAATGA GGAACTGTTA TTTGTATGTG AATTAAAGTG CTCTTATTTT
    AACCATTACT CCTTGACAAT AAACATACAC TTAATTTCAC GAGAATAAAA
```

```
          1870        1880        1890        1900        1910
     TTGGTAATGA  GGAACTGTTA  TTTGTATGTG  AATTAAAGTG  CTCTTATTTT
     AACCATTACT  CCTTGACAAT  AAACATACAC  TTAATTTCAC  GAGAATAAAA
```

FIGURE 7D

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 809
        ( B ) TYPE: NUCLEOTIDE (C) STRANDEDNESS: DOUBLE
(D) TOPOLOGY: UNKNOWN (ii) MOLECULE TYPE: cDNA (xi) SEQUENCE DESCRIPTION:SEQ ID NO:1:

| | | | | |
|---|---|---|---|---|
| AGCGGCGAGG | GCTGGATCCT | GGGCCAAATA | TATGCCAACA | 40 |
| ACGACAAGCT | CTCCAAGAGG | CTGAAGAAAG | TGTGGAAGCC | 80 |
| ACAGCTGTTT | GAGCGAGAGT | TCTACAGTGA | GATCCTGGAC | 120 |
| AAGAAGTTCA | CAGTGACTGT | GACCATGCGG | ACCCTGGACC | 160 |
| TCATCGATGA | GGCTTACGGG | CTCGACTTTT | ACATCCTCAA | 200 |
| GACCCCGAAG | GAGGACCTGT | GCTCCAAGTT | TGGGATGGAG | 240 |
| CTGAAGCGAG | GGATGCTGCT | GCGGCTTGCC | CGGCAGGACC | 280 |
| CCCAGCTGCA | CCCCGAGGAC | CCCGAGCGGC | GGGCAGCCAT | 320 |
| CTACGACAAG | TACAAGGAAT | TTGCCATCCC | AGAGGAGGAG | 360 |
| GCAGAGTGGG | TGGGCCTCAC | GCTGGAGGAG | GCCATTGAGA | 400 |
| AGCAGAGACT | TTTGGAGGAG | AAGGACCCTG | TACCCCTGTT | 440 |
| CAAGATCTAT | GTGGCGGAGC | TGATCCAGCA | GCTGCAGCAG | 480 |
| CAGGCACTGT | CAGAGCCGGC | GGTGGTGCAG | AAGACAGCCA | 520 |
| GTGGCCAGTG | ACCACACAGC | TCCTCCATGC | CTGACCAACA | 560 |
| GGCCCAGCTT | TCCCTGCCAG | GCCCTTTGCA | CTGAGGACAC | 600 |
| AGATCCCGGG | GAGCTGTGAG | GGCCACCGGT | GGGCAGTGGG | 640 |
| TGGATCCTGG | TTTCGTGTGC | TGCCCATGCA | CCTTCCAGCC | 680 |
| CGGGGCCAGC | TTGGCAGGGA | TCCCCAGGAG | GCCTGGGCCG | 720 |
| CCCAGAGGCT | CCTCTCAGGC | TGGGCCCCGA | CGTTTGCGGC | 760 |
| AGTGTTCCTT | GTCCCGTGGG | GCCGGGAGCG | AGTAAAGTCT | 800 |
| GGGCCAGGC | | | | 809 |

(2) INFORMATION FOR SEQ ID NO:2:

(i) SEQUENCE CHARACTERISTICS:
(A) LENGTH: 128
(B) TYPE: AMINO ACID
(C) STRANDEDNESS: UNKNOWN
(D) TOPOLOGY: UNKNOWN (ii) MOLECULE TYPE: PROTEIN (xi) SEQUENCE DESCRIPTION:SEQ ID NO:2:

```
Met Arg Thr Leu Asp Leu Ile Asp Glu Ala Tyr Gly
 1               5                  10

Leu Asp Phe Tyr Ile Leu Lys Thr Pro Lys Glu Asp
            15                  20

Leu Cys Ser Lys Phe Gly Met Glu Leu Lys Arg Gly
25                  30                  35

Met Leu Leu Arg Leu Ala Arg Gln Asp Pro Gln Leu
                40                  45

His Pro Glu Asp Pro Glu Arg Arg Ala Ala Ile Tyr
            50                  55                  60

Asp Lys Tyr Lys Glu Phe Ala Ile Pro Glu Glu Glu
                65                  70
```

```
Ala Glu Trp Val Gly Leu Thr Leu Glu Glu Ala Ile
         75                  80

Glu Lys Gln Arg Leu Leu Glu Glu Lys Asp Pro Val
 85              90                  95

Pro Leu Phe Lys Ile Tyr Val Ala Glu Leu Ile Gln
        100                 105

Gln Leu Gln Gln Gln Ala Leu Ser Glu Pro Ala Val
    110             115                 120

Val Gln Lys Thr Ala Ser Gly Gln
            125
```

( 2 ) INFORMATION FOR SEQ ID NO:3:

( i ) SEQUENCE CHARACTERISTICS:
        ( A ) LENGTH: 24
        ( B ) TYPE: NUCLEOTIDE
        ( C ) STRANDEDNESS: DOUBLE
        ( D ) TOPOLOGY: UNKNOWN ( i i ) MOLECULE TYPE: DNA ( x i ) SEQUENCE DESCRIPTION:SEQ ID NO:3:

CAACAACGAC AAGCTCTCCA AGAG                                      24

( 2 ) INFORMATION FOR SEQ ID NO:4:

( i ) SEQUENCE CHARACTERISTICS:
        ( A ) LENGTH: 20
        ( B ) TYPE: NUCLEOTIDE
        ( C ) STRANDEDNESS: DOUBLE
        ( D ) TOPOLOGY: UNKNOWN ( i i ) MOLECULE TYPE: DNA ( x i ) SEQUENCE DESCRIPTION:SEQ ID NO:4:

GGAACACTGC CGCAAACGTC                                        20

( 2 ) INFORMATION FOR SEQ ID NO:5:

( i ) SEQUENCE CHARACTERISTICS:
        ( A ) LENGTH: 9
        ( B ) TYPE: AMINO ACID
        ( C ) STRANDEDNESS: UNKNOWN
        ( D ) TOPOLOGY: UNKNOWN ( i i ) MOLECULE TYPE: PEPTIDE ( x i ) SEQUENCE DESCRIPTION:SEQ ID NO:5:

```
Ala Tyr Gly Leu Asp Phe Tyr Ile Leu
 1               5
```

( 2 ) INFORMATION FOR SEQ ID NO:6:

( i ) SEQUENCE CHARACTERISTICS:
        ( A ) LENGTH: 10
        ( B ) TYPE: AMINO ACID
        ( C ) STRANDEDNESS: UNKNOWN
        ( D ) TOPOLOGY: UNKNOWN ( i i ) MOLECULE TYPE: PEPTIDE ( x i ) SEQUENCE DESCRIPTION:SEQ ID NO:6:

```
Glu Ala Tyr Gly Leu Asp Phe Tyr Ile Leu
 1               5                   10
```

( 2 ) INFORMATION FOR SEQ ID NO:7:

( i ) SEQUENCE CHARACTERISTICS:
  ( A ) LENGTH: 9
  ( B ) TYPE: AMINO ACID
  ( C ) STRANDEDNESS: UNKNOWN
  ( D ) TOPOLOGY: UNKNOWN ( i i ) MOLECULE TYPE: PEPTIDE ( x i ) SEQUENCE DESCRIPTION:SEQ ID NO:7:

Ala Phe Leu Pro Trp His Arg Leu Phe
 1               5

( 2 ) INFORMATION FOR SEQ ID NO:8:

( i ) SEQUENCE CHARACTERISTICS:
    ( A ) LENGTH: 10
    ( B ) TYPE: AMINO ACID
    ( C ) STRANDEDNESS: UNKNOWN
    ( D ) TOPOLOGY: UNKNOWN ( i i ) MOLECULE TYPE: PEPTIDE ( x i ) SEQUENCE DESCRIPTION:SEQ ID NO:8:

Ala Phe Leu Pro Trp His Arg Leu Phe Leu
 1               5                   1 0

( 2 ) INFORMATION FOR SEQ ID NO:9:

( i ) SEQUENCE CHARACTERISTICS:
    ( A ) LENGTH: 10
    ( B ) TYPE: AMINO ACID
    ( C ) STRANDEDNESS: UNKNOWN
    ( D ) TOPOLOGY: UNKNOWN ( i i ) MOLECULE TYPE: PEPTIDE ( x i ) SEQUENCE DESCRIPTION:SEQ ID NO:9:

Met Phe Asn Asp Ile Asn Ile Tyr Asp Leu
 1               5                   1 0

( 2 ) INFORMATION FOR SEQ ID NO:10:

( i ) SEQUENCE CHARACTERISTICS:
    ( A ) LENGTH: 9
    ( B ) TYPE: AMINO ACID
    ( C ) STRANDEDNESS: UNKNOWN
    ( D ) TOPOLOGY: UNKNOWN ( i i ) MOLECULE TYPE: PEPTIDE ( x i ) SEQUENCE DESCRIPTION:SEQ ID NO:10:

Val Trp Met His Tyr Tyr Val Ser Met
 1               5

( 2 ) INFORMATION FOR SEQ ID NO:11:

( i ) SEQUENCE CHARACTERISTICS:
    ( A ) LENGTH: 9
    ( B ) TYPE: AMINO ACID
    ( C ) STRANDEDNESS: UNKNOWN
    ( D ) TOPOLOGY: UNKNOWN ( i i ) MOLECULE TYPE: PEPTIDE ( x i ) SEQUENCE DESCRIPTION:SEQ ID NO:11:

His Tyr Tyr Val Ser Met Asp Ala Leu
 1               5

( 2 ) INFORMATION FOR SEQ ID NO:12:

( i ) SEQUENCE CHARACTERISTICS:
    ( A ) LENGTH: 10
    ( B ) TYPE: AMINO ACID
    ( C ) STRANDEDNESS: UNKNOWN
    ( D ) TOPOLOGY: UNKNOWN ( i i ) MOLECULE TYPE: PEPTIDE ( x i ) SEQUENCE DESCRIPTION:SEQ ID NO:12:

His Tyr Tyr Val Ser Met Asp Ala Leu Leu
 1                5                     10

( 2 ) INFORMATION FOR SEQ ID NO:13:

( i ) SEQUENCE CHARACTERISTICS:
        ( A ) LENGTH: 9
        ( B ) TYPE: AMINO ACID
        ( C ) STRANDEDNESS: UNKNOWN
        ( D ) TOPOLOGY: UNKNOWN ( i i ) MOLECULE TYPE: PEPTIDE ( x i ) SEQUENCE DESCRIPTION:SEQ ID NO:13:

Tyr Tyr Val Ser Met Asp Ala Leu Leu
 1               5

( 2 ) INFORMATION FOR SEQ ID NO:14:

( i ) SEQUENCE CHARACTERISTICS:
        ( A ) LENGTH: 9
        ( B ) TYPE: AMINO ACID
        ( C ) STRANDEDNESS: UNKNOWN
        ( D ) TOPOLOGY: UNKNOWN ( i i ) MOLECULE TYPE: PEPTIDE ( x i ) SEQUENCE DESCRIPTION:SEQ ID NO:14:

Asp Phe Ala His Glu Ala Pro Ala Phe
 1               5

( 2 ) INFORMATION FOR SEQ ID NO:15:

( i ) SEQUENCE CHARACTERISTICS:
        ( A ) LENGTH: 10
        ( B ) TYPE: AMINO ACID
        ( C ) STRANDEDNESS: UNKNOWN
        ( D ) TOPOLOGY: UNKNOWN ( i i ) MOLECULE TYPE: PEPTIDE ( x i ) SEQUENCE DESCRIPTION:SEQ ID NO:15:

Asp Phe Ala His Glu Ala Pro Ala Phe Leu
 1               5                10

( 2 ) INFORMATION FOR SEQ ID NO:16:

( i ) SEQUENCE CHARACTERISTICS:
        ( A ) LENGTH: 10
        ( B ) TYPE: AMINO ACID
        ( C ) STRANDEDNESS: UNKNOWN
        ( D ) TOPOLOGY: UNKNOWN ( i i ) MOLECULE TYPE: PEPTIDE ( x i ) SEQUENCE DESCRIPTION:SEQ ID NO:16:

Pro Trp His Arg Leu Phe Leu Leu Arg Trp
 1               5                10

( 2 ) INFORMATION FOR SEQ ID NO:17:

( i ) SEQUENCE CHARACTERISTICS:
  ( A ) LENGTH: 10
  ( B ) TYPE: AMINO ACID
  ( C ) STRANDEDNESS: UNKNOWN
  ( D ) TOPOLOGY: UNKNOWN ( i i ) MOLECULE TYPE: PEPTIDE ( x i ) SEQUENCE DESCRIPTION:SEQ ID NO:17:

Leu Phe Leu Leu Arg Trp Glu Gln Glu Ile
 1     5       10

( 2 ) INFORMATION FOR SEQ ID NO:18:

( i ) SEQUENCE CHARACTERISTICS:
  ( A ) LENGTH: 1910
  ( B ) TYPE: NUCLEOTIDE
  ( C ) STRANDEDNESS: DOUBLE
  ( D ) TOPOLOGY: UNKNOWN ( i i ) MOLECULE TYPE: PEPTIDE ( x i ) SEQUENCE DESCRIPTION:SEQ ID NO:18:

| Sequence | | | | Position |
|---|---|---|---|---|
| TGCAGACCTT | GTGAGGACTA | GAGGAAGAAT | GCTCCTGGCT | 40 |
| GTTTTGTACT | GCCTGCTGTG | GAGTTTCCAG | ACCTCCGCTG | 80 |
| GCCATTTCCC | TAGTGCCTGT | GTCTCCTCTA | AGAACCTGAT | 120 |
| GGAGAAGGAA | TGCTGTCCAC | CGTGGAGCGG | GGACAGGAGT | 160 |
| CCCTGTGGCC | AGCTTTCAGG | CAGAGGTTCC | TGTCAGAATA | 200 |
| TCCTTCTGTC | CAATGCACCA | CTTGGGCCTC | AATTTCCCTT | 240 |
| CACAGGGGTG | GATGACGGG | AGTCGTGGCC | TTCCGTCTTT | 280 |
| TATAATAGGA | CCTGCCAGTG | CTCTGGCAAC | TTCATGGGAT | 320 |
| TCAACTGTGG | AAACTGCAAG | TTTGGCTTTT | GGGGACCAAA | 360 |
| CTGCACAGAG | AGACGACTCT | TGGTGAGAAG | AAACATCTTC | 400 |
| GATTTGAGTG | CCCCAGAGAA | GGACAAATTT | TTTGCCTACC | 440 |
| TCACTTTAGC | AAAGCATACC | ATCAGCTCAG | ACTATGTCAT | 480 |
| CCCCATAGGG | ACCTATGGCC | AAATGAAAAA | TGGATCAACA | 520 |
| CCCATGTTTA | ACGACATCAA | TATTTATGAC | CTCTTTGTCT | 560 |
| GGATGCATTA | TTATGTGTCA | ATGGATGCAC | TGCTTGGGGG | 600 |
| ATCTGAAATC | TGGAGAGACA | TTGATTTTGC | CCATGAAGCA | 640 |
| CCAGCTTTTC | TGCCTTGGCA | TAGACTCTTC | TTGTTGCGGT | 680 |
| GGGAACAAGA | AATCCAGAAG | CTGACAGGAG | ATGAAAACTT | 720 |
| CACTATTCCA | TATTGGGACT | GGCGGGATGC | AGAAAAGTGT | 760 |
| GACATTTGCA | CAGATGAGTA | CATGGGAGGT | CAGCACCCCA | 800 |
| CAAATCCTAA | CTTACTCAGC | CCAGCATCAT | TCTTCTCCTC | 840 |
| TTGGCAGATT | GTCTGTAGCC | GATTGGAGGA | GTACAACAGC | 880 |
| CATCAGTCTT | TATGCAATGG | AACGCCCGAG | GGACCTTTAC | 920 |
| GGCGTAATCC | TGGAAACCAT | GACAAATCCA | GAACCCCAAG | 960 |
| GCTCCCCTCT | TCAGCTGATG | TAGAATTTTG | CCTGAGTTTG | 1000 |
| ACCCAATATG | AATCTGGTTC | CATGGATAAA | GCTGCCAATT | 1040 |
| TCAGCTTTAG | AAATACACTG | GAAGGATTTG | CTAGTCCACT | 1080 |

| | | |
|---|---|---|
| TACTGGGATA GCGGATGCCT CTCAAAGCAG CATGCACAAT | 1120 |
| GCCTTGCACA TCTATATGAA TGGAACAATG TCCCAGGTAC | 1160 |
| AGGGATCTGC CAACGATCCT ATCTTCCTTC TTCACCATGC | 1200 |
| ATTTGTTGAC AGTATTTTTG AGCAGTGGCT CCGAAGGCAC | 1240 |
| CGTCCTCTTC AAGAAGTTTA TCCAGAAGCC AATGCACCCA | 1280 |
| TTGGACATAA CCGGGAATCC TACATGGTTC CTTTTATACC | 1320 |
| ACTGTACAGA AATGGTGATT TCTTTATTTC ATCCAAAGAT | 1360 |
| CTGGGCTATG ACTATAGCTA TCTACAAGAT TCAGACCCAG | 1400 |
| ACTCTTTTCA AGACTACATT AAGTCCTATT TGGAACAAGC | 1440 |
| GAGTCGGATC TGGTCATGGC TCCTTGGGGC GGCGATGGTA | 1480 |
| GGGGCCGTCC TCACTGCCCT GCTGGCAGGG CTTGTGAGCT | 1520 |
| TGCTGTGTCG TCACAAGAGA AAGCAGCTTC CTGAAGAAAA | 1560 |
| GCAGCCACTC CTCATGGAGA AAGAGGATTA CCACAGCTTG | 1600 |
| TATCAGAGCC ATTTATAAAA GGCTTAGGCA ATAGAGTAGG | 1640 |
| GCCAAAAAGC CTGACCTCAC TCTAACTCAA AGTAATGTCC | 1680 |
| AGGTTCCCAG AGAATATCTG CTGGTATTTT TCTGTAAAGA | 1720 |
| CCATTTGCAA AATTGTAACC TAATACAAAG TGTAGCCTTC | 1760 |
| TTCCAACTCA GGTAGAACAC ACCTGTCTTT GTCTTGCTGT | 1800 |
| TTTCACTCAG CCCTTTTAAC ATTTTCCCCT AAGCCCATAT | 1840 |
| GTCTAAGGAA AGGATGCTAT TTGGTAATGA GGAACTGTTA | 1880 |
| TTTGTATGTG AATTAAAGTG CTCTTATTTT | 1910 |

( 2 ) INFORMATION FOR SEQ ID NO:19:

( i ) SEQUENCE CHARACTERISTICS:
        ( A ) LENGTH: 529
        ( B ) TYPE: AMINO ACID
        ( C ) STRANDEDNESS: UNKNOWN
        ( D ) TOPOLOGY: UNKNOWN ( i i ) MOLECULE TYPE: PROTEIN ( x i ) SEQUENCE DESCRIPTION:SEQ ID NO:19:

Met Leu Leu Ala Val Leu Tyr Cys Leu Leu Trp Ser
 1              5                    10

Phe Gln Thr Ser Ala Gly His Phe Pro Ser Ala Cys
         15                   20

Val Ser Ser Lys Asn Leu Met Glu Lys Glu Cys Cys
 25              30                35

Pro Pro Trp Ser Gly Asp Arg Ser Pro Cys Gly Gln
         40                 45

Leu Ser Gly Arg Gly Ser Cys Gln Asn Ile Leu Leu
     50            55              60

Ser Asn Ala Pro Leu Gly Pro Gln Phe Pro Phe Thr
         65                 70

Gly Val Asp Asp Arg Glu Ser Trp Pro Ser Val Phe
       75              80

Tyr Asn Arg Thr Cys Gln Cys Ser Gly Asn Phe Met
 85              90                95

Gly Phe Asn Cys Gly Asn Cys Lys Phe Gly Phe Trp

|     |     |     |     |     |     |     |     |     |     |
| --- | --- | --- | --- | --- | --- | --- | --- | --- | --- |
|     |     |     | 100 |     |     |     | 105 |     |     |
| Gly | Pro | Asn | Cys | Thr | Glu | Arg | Arg | Leu | Leu | Val | Arg |
|     | 110 |     |     |     | 115 |     |     |     | 120 |
| Arg | Asn | Ile | Phe | Asp | Leu | Ser | Ala | Pro | Glu | Lys | Asp |
|     |     |     | 125 |     |     |     | 130 |
| Lys | Phe | Phe | Ala | Tyr | Leu | Thr | Leu | Ala | Lys | His | Thr |
|     |     | 135 |     |     |     | 140 |
| Ile | Ser | Ser | Asp | Tyr | Val | Ile | Pro | Ile | Gly | Thr | Tyr |
| 145 |     |     |     |     | 150 |     |     |     | 155 |
| Gly | Gln | Met | Lys | Asn | Gly | Ser | Thr | Pro | Met | Phe | Asn |
|     |     |     | 160 |     |     |     | 165 |
| Asp | Ile | Asn | Ile | Tyr | Asp | Leu | Phe | Val | Trp | Met | His |
|     | 170 |     |     |     | 175 |     |     |     | 180 |
| Tyr | Tyr | Val | Ser | Met | Asp | Ala | Leu | Leu | Gly | Gly | Ser |
|     |     |     |     | 185 |     |     |     | 190 |
| Glu | Ile | Trp | Arg | Asp | Ile | Asp | Phe | Ala | His | Glu | Ala |
|     |     | 195 |     |     |     | 200 |
| Pro | Ala | Phe | Leu | Pro | Trp | His | Arg | Leu | Phe | Leu | Leu |
| 205 |     |     |     |     | 210 |     |     |     | 215 |
| Arg | Trp | Glu | Gln | Glu | Ile | Gln | Lys | Leu | Thr | Gly | Asp |
|     |     |     | 220 |     |     |     | 225 |
| Glu | Asn | Phe | Thr | Ile | Pro | Tyr | Trp | Asp | Trp | Arg | Asp |
|     | 230 |     |     |     | 235 |     |     |     | 240 |
| Ala | Glu | Lys | Cys | Asp | Ile | Cys | Thr | Asp | Glu | Tyr | Met |
|     |     |     | 245 |     |     |     | 250 |
| Gly | Gly | Gln | His | Pro | Thr | Asn | Pro | Asn | Leu | Leu | Ser |
|     |     | 255 |     |     |     | 260 |
| Pro | Ala | Ser | Phe | Phe | Ser | Ser | Trp | Gln | Ile | Val | Cys |
| 265 |     |     |     | 270 |     |     |     |     | 275 |
| Ser | Arg | Leu | Glu | Glu | Tyr | Asn | Ser | His | Gln | Ser | Leu |
|     |     |     | 280 |     |     |     | 285 |
| Cys | Asn | Gly | Thr | Pro | Glu | Gly | Pro | Leu | Arg | Arg | Asn |
|     | 290 |     |     |     | 295 |     |     |     | 300 |
| Pro | Gly | Asn | His | Asp | Lys | Ser | Arg | Thr | Pro | Arg | Leu |
|     |     |     | 305 |     |     |     | 310 |
| Pro | Ser | Ser | Ala | Asp | Val | Glu | Phe | Cys | Leu | Ser | Leu |
|     |     | 315 |     |     |     | 320 |
| Thr | Gln | Tyr | Glu | Ser | Gly | Ser | Met | Asp | Lys | Ala | Ala |
| 325 |     |     |     |     | 330 |     |     |     | 335 |
| Asn | Phe | Ser | Phe | Arg | Asn | Thr | Leu | Glu | Gly | Phe | Ala |
|     |     |     | 340 |     |     |     | 345 |
| Ser | Pro | Leu | Thr | Gly | Ile | Ala | Asp | Ala | Ser | Gln | Ser |
|     | 350 |     |     |     | 355 |     |     |     | 360 |
| Ser | Met | His | Asn | Ala | Leu | His | Ile | Tyr | Met | Asn | Gly |
|     |     |     | 365 |     |     |     | 370 |
| Thr | Met | Ser | Gln | Val | Gln | Gly | Ser | Ala | Asn | Asp | Pro |
|     |     | 375 |     |     |     | 380 |
| Ile | Phe | Leu | Leu | His | His | Ala | Phe | Val | Asp | Ser | Ile |
| 385 |     |     |     |     | 390 |     |     |     | 395 |
| Phe | Glu | Gln | Trp | Leu | Arg | Arg | His | Arg | Pro | Leu | Gln |
|     |     |     | 400 |     |     |     | 405 |
| Glu | Val | Tyr | Pro | Glu | Ala | Asn | Ala | Pro | Ile | Gly | His |
|     | 410 |     |     |     | 415 |     |     |     | 420 |

| Asn | Arg | Glu | Ser | Tyr<br>425 | Met | Val | Pro | Phe | Ile<br>430 | Pro | Leu |
|---|---|---|---|---|---|---|---|---|---|---|---|
| Tyr | Arg | Asn<br>435 | Gly | Asp | Phe | Phe | Ile<br>440 | Ser | Ser | Lys | Asp |
| Leu<br>445 | Gly | Tyr | Asp | Tyr | Ser<br>450 | Tyr | Leu | Gln | Asp | Ser<br>455 | Asp |
| Pro | Asp | Ser | Phe<br>460 | Gln | Asp | Tyr | Ile | Lys<br>465 | Ser | Tyr | Leu |
| Glu | Gln<br>470 | Ala | Ser | Arg | Ile | Trp<br>475 | Ser | Trp | Leu | Leu | Gly<br>480 |
| Ala | Ala | Met | Val | Gly<br>485 | Ala | Val | Leu | Thr | Ala<br>490 | Leu | Leu |
| Ala | Gly | Leu<br>495 | Val | Ser | Leu | Leu | Cys<br>500 | Arg | His | Lys | Arg |
| Lys<br>505 | Gln | Leu | Pro | Glu | Glu<br>510 | Lys | Gln | Pro | Leu | Leu<br>515 | Met |
| Glu | Lys | Glu | Asp<br>520 | Tyr | His | Ser | Leu | Tyr<br>525 | Gln | Ser | His |
| Leu | | | | | | | | | | | |

( 2 ) INFORMATION FOR SEQ ID NO:20:

( i ) SEQUENCE CHARACTERISTICS:
        ( A ) LENGTH: 100
        ( B ) TYPE: NUCLEOTIDE
        ( C ) STRANDEDNESS: DOUBLE
        ( D ) TOPOLOGY: UNKNOWN ( i i ) MOLECULE TYPE: cDNA ( x i ) SEQUENCE DESCRIPTION:SEQ ID NO:20:

| ATGCGGACCC | TGGACCTCAT | CGATGAGGCT | TACGGGCTCG | 40 |
| ACTTTTACAT | CCTCAAGACC | CCGAAGGAGG | ACCTGTGCTC | 80 |
| CAAGTTTGGG | ATGGAGCTGA | | | 100 |

( 2 ) INFORMATION FOR SEQ ID NO:21:

( i ) SEQUENCE CHARACTERISTICS:
        ( A ) LENGTH: 33
        ( B ) TYPE: AMINO ACID
        ( C ) STRANDEDNESS: UNKNOWN
        ( D ) TOPOLOGY: UNKNOWN ( i i ) MOLECULE TYPE: PROTEIN ( x i ) SEQUENCE DESCRIPTION:SEQ ID NO:21:

| Met<br>1 | Arg | Thr | Leu | Asp<br>5 | Leu | Ile | Asp | Glu | Ala<br>10 | Tyr | Gly |
|---|---|---|---|---|---|---|---|---|---|---|---|
| Leu | Asp | Phe<br>15 | Tyr | Ile | Leu | Lys | Thr<br>20 | Pro | Lys | Glu | Asp |
| Leu<br>25 | Cys | Ser | Lys | Phe | Gly<br>30 | Met | Glu | Leu | | | |

( 2 ) INFORMATION FOR SEQ ID NO:22:

( i ) SEQUENCE CHARACTERISTICS:
        ( A ) LENGTH: 100
        ( B ) TYPE: NUCLEOTIDE
        ( C ) STRANDEDNESS: DOUBLE
        ( D ) TOPOLOGY: UNKNOWN ( i i ) MOLECULE TYPE: cDNA (x i) SEQUENCE DESCRIPTION:SEQ ID NO:22:

ATGCGGACCC TGGACCTCAT CAATGAGGCT TACGGGCTCG           40

ACTTTTACAT CCTCAGGCTG GGCCCCGACG TTTGCGGCAG           80

TGTTCCTTGT CCCGTGGGGC                                100

(2) INFORMATION FOR SEQ ID NO:23:

(i) SEQUENCE CHARACTERISTICS:
        (A) LENGTH: 33
        (B) TYPE: AMINO ACID
        (C) STRANDEDNESS: UNKNOWN
        (D) TOPOLOGY: UNKNOWN (ii) MOLECULE TYPE: cDNA (x i) SEQUENCE DESCRIPTION:SEQ ID NO:23:

Met Arg Thr Leu Asp Leu Ile Asn Glu Ala Tyr Gly
 1               5                  10

Leu Asp Phe Tyr Ile Leu Arg Leu Gly Pro Asp Val
            15              20

Cys Gly Ser Val Pro Cys Pro Val Gly
 25                  30

P15 AND TYROSINASE MELANOMA ANTIGENS AND THEIR USE IN DIAGNOSTIC AND THERAPEUTIC METHODS

FIELD OF THE INVENTION

This invention is in the field of prevention and treatment of human cancers. More specifically, this invention relates to the p15 gene which encodes melanoma antigens recognized by T-Cells and their corresponding proteins and to preventative, diagnostic and therapeutic applications which employ these genes, proteins or peptides. This invention also relates to preventative, diagnostic or therapeutic applications utilizing tyrosinase peptides which encode melanoma antigens.

BACKGROUND OF THE INVENTION

Melanomas are aggressive, frequently metastatic tumors derived from either melanocytes or melanocyte related nevus cells ("Cellular and Molecular Immunology" (1991) (eds) Abbas A. K., Lechtman, A. H., Pober, J. S.; W. B. Saunders Company, Philadelphia: pages 340–341). Melanomas make up approximately three percent of all skin cancers and the worldwide increase in melanoma is unsurpassed by any other neoplasm with the exception of lung cancer in women ("Cellular and Molecular Immunology" (1991) (eds) Abbas, A. K., Lechtiman, A. H., Pober, J. S.; W. B. Saunders Company Philadelphia pages: 340–342; Kirkwood and Agarwala (1993) *Principles and Practice of Oncoloqy* 7:1–16). Even when melanoma is apparently localized to the skin, up to 30% of the patients will develop systemic metastasis and the majority will die (Kirkwood and Agarwala (1993) *Principles and Practice of Oncoloqy* 7:1–16). Classic modalities of treating melanoma include surgery, radiation and chemotherapy. In the past decade immunotherapy and gene therapy have emerged as new and promising methods for treating melanoma.

T cells play an important role in tumor regression in most murine tumor models. Tumor infiltrating lymphocytes (TIL) that recognize unique cancer antigens can be isolated from many murine tumors. The adoptive transfer of these TIL plus interleukin-2 can mediate the regression of established lung and liver metastases (Rosenberg, S. A., et al., (1986) *Science* 233:1318–1321). In addition, the secretion of IFN-γ by injected TIL significantly correlates with in vivo regression of murine tumors suggesting activation of T-cells by the tumor antigens. (Barth, R. J., et al., (1991) *J. Exo. Med.* 173:647–658). The known ability of tumor TIL to mediate the regression of metastatic cancer in 35 to 40% of melanoma patients when adoptively transferred into patients with metastatic melanoma attests to the clinical importance of the antigens recognized (Rosenberg, S. A., et al., (1988) *N Enql J Med* 319:1676–1680; Rosenberg S. A. (1992) *J. Clin. Oncol.* 10:180–199).

T cell receptors on CD8$^+$ T cells recognize a complex consisting of an antigenic peptide (9–10 amino acids for HLA-A2), β-2microglobulin and class I major histocompatibility complex (MHC) heavy chain (HLA-A, B, C, in humans). Peptides generated by digestion of endogenously synthesized proteins are transported into the endoplastic reticulum, bound to class I MHC heavy chain and β2 microglobulin, and finally expressed in the cell surface in the groove of the class I MHC molecule. Therefore, T cells can detect molecules that originate from proteins inside cells, in contrast to antibodies that detect intact molecules expressed on the cell surface. Therefore, antigens recognized by T cells may be more useful than antigens recognized by antibodies.

Strong evidence that an immune response to cancer exists in humans is provided by the existence of lymphocytes within melanoma deposits. These lymphocytes, when isolated, are capable of recognizing specific tumor antigens on autologous and allogeneic melanomas in an MHC restricted fashion. (Itoh, K. et al. (1986), *Cancer Res.* 46: 3011–3017; Muul, L. M., et al. (1987), *J. Immunol.* 138:989–995); Topalian, S. L., et al., (1989) *J. Immunol.* 142: 3714–3725; Darrow, T. L., et al., (1989) *J. Immunol.* 142: 3329–3335; Hom, S. S., et al., (1991) *J. Immunother.* 10:153–164; Kawakami, Y., et al., (1992) *J. Immunol.* 148: 638–643; Hom, S. S., et al., (1993) *J. Immunother.* 13:18–30; O'Neil, B. H., et al., (1993) *J. Immunol.* 151: 1410–1418). TIL from patients with metastatic melanoma recognize shared antigens including melanocyte-melanoma lineage specific tissue antigens in vitro (Kawakami, Y., et al., (1993) *J. Immunother.* 14: 88–93; Anichini, A. et al., (1993) et al., *J. Exp. Med.* 177: 989–998). Anti-melanoma T cells appear to be enriched in TIL probably as a consequence of clonal expansion and accumulation at the tumor site in vivo (Sensi, M., et al., (1993) *J. Exp. Med.* 178:1231–1246). The fact that many melanoma patients mount cellular and humoral responses against these tumors and that melanomas express both MHC antigens and tumor associated antigens (TAA) suggests that identification and characterization of additional melanoma antigens will be important for immunotherapy of patients with melanoma.

Peripheral blood lymphocytes have been used to identify potential melanoma tumor antigens. Van Der Bruggen et al. (1991) *Science* 254: 1643–1647 has characterized a gene coding for a melanoma antigen, designated MAGE-1, using T cell clones established from the peripheral blood of patients who were repetitively immunized in vivo with mutagenized tumor cells and was found to belong to a previously undescribed multi-gene family (Gaugler, B. et al., (1994) *J. Exp. Med.* 179:921). Cytotoxic T-cells derived from the peripheral blood lymphocytes (PBL) of patients with melanoma were used to identify a potential antigenic peptide encoding MAGE-1 (Traversari, C., et al. (1992) *J. Exp. Med.* 176:1453–1457). Brichard et al. (1993) *J. Exp. Med.* 178:489–495 has also characterized a gene encoding a melanoma antigen designated tyrosinase using peripheral blood lymphocytes from patients who were sensitized by repetitive in vitro stimulation with tumor. A melanoma antigen designated MAGE-3 was identified using T-cells from PBL of a patient who had been repeatedly immunized with autologous tumor, and were recognized by HLA-A1-restricted CTL (Van der Bruggen, P., et al., (1991) *Science* (Washington D.C.), 254: 1643–1647; Gaugler, B., et al., (1994) *J. Exp. Med.*, 197: 921–930). Melanoma antigens MART-1 and gp100 have been recently cloned and were recognized by HLA-A2-restricted TIL (Kawakami, Y., (1994) *Proc. Natl. Acad. Sci.* (*USA*.), 91:6458–6462; Bakker, A. B. H., et al., (1994) *J. Exp. Med.*, 179: 1005–1009; Kawakami, Y., (1994) et al., *Proc. Natl. Acad. Sci.* (*USA*), 91: 3515–3519.) Both MART-1 and gp100 are specifically expressed in melanoma and melanocytes. Further support for the therapeutic potential of melanoma antigens is provided by Brown et al. (U.S. Pat. No. 5,262, 177). Brown et al. (U.S. Pat. No. 5,262,177) relates to a recombinant vaccinia virus-based melanoma vaccine where the melanoma antigen p97 is reported to show a protective effect from tumor cell challenge in both murine models. Characterization of additional melanoma antigens is important for the development of new strategies for cancer immunotherapy, in particular for melanoma.

SUMMARY OF THE INVENTION

This invention relates, in general, to a nucleic acid sequence, encoding melanoma antigens recognized by T-lymphocytes and protein and peptides encoded by these sequences. This invention further provides bioassays for these nucleic acid sequences, proteins and peptides. This invention also provides therapeutic uses for the nucleic acid sequences, proteins or peptides described herein.

It is a general object of the present invention to provide a substantially purified and isolated nucleic acid sequence which encodes for the p15 melanoma antigen.

It is another object of this invention to provide a recombinant molecule comprising a vector and all or part of the nucleic acid sequence encoding p15.

It is another object of this invention to produce recombinant proteins encoded by all or part of the nucleic acid sequence encoding p15.

It is a further object of this invention to provide monoclonal or polyclonal antibodies reactive with the p15 protein, peptides or portions thereof.

It is an object of this invention to provide methods of detecting the p15 gene or p15 mRNA in a biological sample.

It is another object of this invention to provide methods of detecting the p15 protein or peptides in a biological sample.

It is an object of this invention to provide diagnostic methods for human disease, in particular for melanomas and metastatic melanomas.

It is a further object of this invention to provide methods for prophylactic or therapeutic uses involving all or part of the nucleic acid sequence encoding p15 and its corresponding protein or peptides derived from the p15 amino acid sequence.

It is also an object of this invention to provide melanoma vaccines comprising all or part of the nucleic acid sequence encoding p15 or its corresponding protein for preventing or treating melanoma.

It is a further object of this invention to provide immunogenic peptides derived from the p15 protein sequence for use in vaccines.

In addition, it is another object of this invention to provide multivalent vaccines comprising all or part of the p15 nucleic acid sequence or its corresponding protein or peptides and at least one other immunogenic molecule capable of eliciting the production of antibodies in a mammal to melanoma antigens.

It is another object of this invention to provide a method for preventing or treating melanoma utilizing all or part of the p15 nucleic acid sequence or its corresponding protein in gene therapy protocols.

It is a further object of this invention to provide immunogenic peptides derived from a tyrosinase protein sequence for use in vaccines.

It is yet another object of this invention to provide a method of prophylactic or therapeutic immunization for melanoma using the vaccines described herein.

It is a further object of this invention to provide a method of identifying melanoma antigens that would constitute potential targets for immunotherapy.

DESCRIPTION OF THE FIGURES

FIG. 1 shows the sequence of the p15 cDNA clone (SEQ ID NO:1). The longest open reading frame was translated, beginning with the first in frame methionine (SEQ ID NO:2).

FIG. 3 shows partial sequences of clones (SEQ ID NO:20 and 22) isolated by RT-PCR from EBV B cell RNA. The sequence of the clones (SEQ ID NO:21 and 23) beginning with the first methionine of the coding region was compared with the sequence of p15. Identical residues are indicated by dots.

FIGS. 7A through 7D show the tyrosinase nucleic acid (SEQ ID NO:18) and amino acid sequence (SEQ ID NO:19) (single letter code).

DETAILED DESCRIPTION OF THE INVENTION

Figure 2:
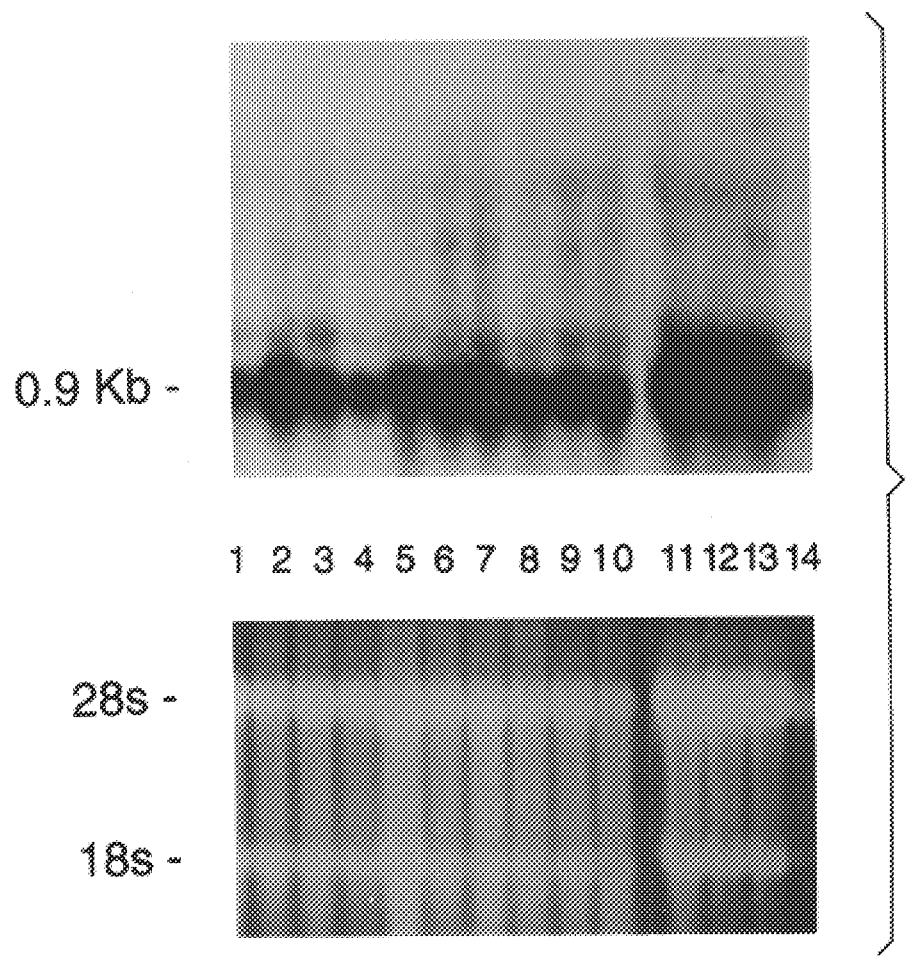
FIG. 2 shows RNA from normal human spleen (lane 1), testes (lane 2), thymus (lane 3), fetal liver (lane 4), liver (lane 5), kidney (lane 6), brain (lane 7), adrenal gland (lane 8), lung (lane 9), retina (lane 10), 1290 mel (lane 11), 501 mel (lane 12), 888 mel (lane 13), and 888 EBV B (lane 14) which were probed with a fragment of p15 as described in the Materials and Methods in Example 1 (upper panel). The gel was stained with ethidium bromide as a control for loading (lower panel).

For the purpose of a more complete understanding of the invention, the following definitions are described herein. Nucleic acid sequences includes, but is not limited to, DNA, RNA or cDNA. Nucleic acid sequence as used herein refers to an isolated nucleic acid sequence. p15 messenger RNA (mRNA) refers to one or more RNA transcripts which are a product of the p15 gene. Substantially homologous as used herein refers to substantial correspondence between the nucleic acid sequence of p15 shown in FIG. 1 (SEQ ID NO:1) and that of any other nucleic acid sequence. Substantially homologous means about 50–100% homologous homology, preferably by about 70–100% homology, and most preferably about 90–100% homology between the p15 sequence and that of any other nucleic acid sequence. In addition, substantially homologous as used herein also refers to substantial correspondences between the amino acid sequence of the p15 antigen shown in FIG. 1 (SEQ ID NO: 2) and that of any other amino acid sequence.

Major Histocompatibility Complex (MHC) is a generic designation meant to encompass the histo-compatibility antigen systems described in different species including the human leucocyte antigens (HLA).

The term melanoma includes, but is not limited to, melanomas, metastatic melanomas, melanomas derived from either melanocytes or melanocytes related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma or familial atypical mole and melanoma (FAM-M) syndrome. Such melanomas in mammals may be caused by, chromosomal abnormalities, degenerative growth and developmental disorders, mitogenic agents, ultraviolet radiation (UV), viral infections, inappropriate tissue expression of a gene, alterations in expression of a gene, and presentation on a cell, or carcinogenic agents. The aforementioned melanomas can be diagnosed, assessed or treated by methods described in the present application.

By atypical mole we mean a mole with features that are abnormal and may be precancerous.

By melanoma antigen or immunogen we mean all or parts thereof of the p15 protein or peptides based on the p15 protein sequence capable of causing a cellular or humoral immune response in a mammal. Such antigens may also be reactive with antibodies from animals immunized with all, part or parts of the p15 protein (FIG. 1; SEQ ID NO:2). Such a protein or peptide may be encoded by all or part of the p15 nucleic acid sequence of this invention.

By immunogenic peptide we mean a peptide derived from the p15 protein sequence (FIG. 1; SEQ ID NO:2) or the tyrosinase peptides (SEQ ID NO:7 and SEQ ID NO:8) capable of causing a cellular or humoral immune response in a mammal. Such peptides may also be reactive with antibodies from an animal immunized with the peptides. Such peptides may be about 5–20 amino acid in length preferably about 8 to 15 amino acids in length, and most preferably about 9–10 amino acids in length.

One skilled in the art will understand that the bioassays of the present invention may be used in the analysis of biological samples or tissues from any vertebrate species. In a preferred embodiment, mammalian biological samples or tissues are analyzed.

Tissue includes, but is not limited to, single cells, whole organs and portions thereof. Biological samples include, but are not limited to, tissues, primary cultures of mammalian tissues, biopsy specimens, pathology specimens, and necropsy specimens. Mammal includes but is not limited to, humans, monkeys, dogs, cats, mice, rats, pigs, cows, pigs, horses, sheep and goats.

The present invention provides a nucleic acid sequence which encodes a novel melanoma antigen recognized by T cells. The gene encoding this novel melanoma antigen is designated p15. The p15 cDNA shows no significant homology to any known melanoma antigen or protein and thus represents a gene encoding a new melanoma antigen. The only long open reading frame in this cDNA encodes a 128 amino acid polypeptide with a molecular weight (MW) of approximately 15 kilodaltons (kd) beginning with the first in frame methionine. p15 does not appear to contain any features which would identify it as a member of any known gene family, and lacks a conventional leader sequence, as well as consensus sites for N-linked glycosylation and any extended hydrophobic domains.

p15 RNA is expressed in cultured melanoma and melanocyte cell lines and a wide variety of human tissues such as retina, testis, and brain. The cDNA sequence for p15 is shown in FIG. 1 (SEQ ID NO:1), the deduced amino acid sequence for the p15 protein is also shown in FIG. 1 (SEQ ID NO:1).

The nucleic acid sequence for p15 shown in FIG. 1 (SEQ ID NO:1), represents a preferred embodiment of the invention. It is, however, understood by one skilled in the art that due to the degeneracy of the genetic code variations in the cDNA sequence shown in FIG. 1 (SEQ ID NO:1) will still result in a DNA sequence capable of encoding the p15 protein antigen. Such DNA sequences are therefore functionally equivalent to the sequence set forth in FIG. 1 (SEQ ID NO:1) and are intended to be encompassed within the present invention. Further, a person of skill in the art will understand that there are naturally occurring allelic variations in a given species of the p15 nucleic acid sequence shown in FIG. 1 (SEQ ID NO:1), these variations are also intended to be encompassed by the present invention. Also intended to be encompassed within this invention are nucleic acid sequences which are complimentary to nucleic acid sequences capable of hybridizing to the p15 nucleic acid sequence shown in FIG. 1 under low stringency conditions. One of skill in the art will understand what it is meant by low stringency conditions and the modifications necessary to obtain low stringency conditions. Elements that can be varied to effect stringency include, but are not limited to, salt concentrations or temperature.(Ausubel et al., (1987) in "Current Protocols in Molecular Biology", John Wiley and Sons, New York, N.Y.).

This invention further includes p15 protein or peptides or analogs thereof having substantially the same function as the p15 antigen or protein of this invention. Such proteins or polypeptides include, but are not limited to, a fragment of the protein, or a substitution, addition or deletion mutant of the p15 protein. This invention also encompasses proteins or peptides that are substantially homologous to the p15 antigen. The term "analog" includes any polypeptide having an amino acid residue sequence substantially identical to the p15 sequence specifically shown herein (FIG. 1; SEQ ID NO:2) in which one or more residues have been conservatively substituted with a functionally similar residue and which displays the functional aspects of the p15 antigen as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

The phrase "conservative substitution" also includes the use of a chemically derivatized residue in place of a non-derivatized residue. "Chemical derivative" refers to a subject polypeptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those proteins or peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Proteins or polypeptides of the present invention also include any polypeptide having one or more additions and/or deletions or residues relative to the sequence of a polypeptide whose sequence is encoded is the DNA of p15, so long as the requisite activity is maintained.

This invention also provides a recombinant DNA molecule comprising all or part of the p15 nucleic acid sequence (SEQ ID NO:1) and a vector. Expression vectors suitable for use in the present invention comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, retrovirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology", John Wiley and Sons, New York, N.Y.) or commercially available.

Another aspect of this invention relates to a host organism into which recombinant expression vector containing all or part of the p15 nucleic acid sequence has been inserted. The host cells transformed with the p15 nucleic acid sequence of this invention includes eukaryotes, such as animal, plant, insect and yeast cells and prokaryotes, such as *E. coli*. The means by which the vector carrying the gene may be introduced into the cell include, but are not limited to, microinjection, electroporation, transduction, or transfection using DEAE-dextran, lipofection, calcium phosphate or other procedures known to one skilled in the art (Sambrook et al. (1989) in "Molecular Cloning. A Laboratory Manual", Cold Spring Harbor Press, Plainview, N.Y.).

In a preferred embodiment, eukaryotic expression vectors that function in eukaryotic cells are used. Examples of such vectors include, but are not limited to, retroviral vectors, vaccinia virus vectors, adenovirus vectors, herpes virus vector, fowl pox virus vector, plasmids, such as pCDNA3 (Invitrogen, San Diego, Calif.) or the baculovirus transfer vectors. Preferred eukaryotic cell lines include, but are not limited to, COS cells, CHO cells, HeLa cells, NIH/3T3 cells, 293 cells (ATCC# CRL1573), T2 cells, dendritic cells, or monocytes. In a preferred embodiment the recombinant p15 protein expression vector is introduced into mammalian cells, such as NIH/3T3, COS-7, CHO, 293 cells (ATCC #CRL 1573), T2 cells, dendritic cells, or monocytes to ensure proper processing and modification of the p15 protein. By way of example, the p15 cDNA is introduced into COS7 cells (Gluzman, Y. et al. (1981) *Cell* 23: 175–182) to be expressed.

In one embodiment the expressed recombinant p15 protein may be detected by methods known in the art which include Coomassie blue staining and Western blotting using antibodies specific for the p15 protein.

In a further embodiment, the recombinant protein expressed by the host cells can be obtained as a crude lysate or can be purified by standard protein purification procedures known in the art which may include differential precipitation, molecular sieve chromatography, ion-exchange chromatography, isoelectric focusing, gel electrophoresis, affinity, and immunoaffinity chromatography and the like. (Ausubel et. al., (1987) in "Current Protocols in Molecular Biology" John Wiley and Sons, New York, N.Y.). In the case of immunoaffinity chromatography, the recombinant protein may be purified by passage through a column containing a resin which has bound thereto antibodies specific for the p15 protein (Ausubel et. al., (1987) in "Current Protocols in Molecular Biology" John Wiley and Sons, New York, N.Y.).

The nucleic acid sequence or portions thereof, of this invention are useful as probes for the detection of expression of the p15 gene in normal and diseased tissue. Therefore, another aspect of the present invention relates to a bioassay for detecting messenger RNA encoding the p15 protein in a biological sample comprising the steps of (a) contacting a biological sample with all or part of the nucleic acid sequence of this invention under conditions allowing a complex to form between said nucleic acid sequence and said messenger RNA, and (b) detecting said complexes. This method may further comprise a step (c) of determining the level of said messenger RNA.

RNA can be isolated as whole cell RNA or as poly(A)$^+$ RNA. Whole cell RNA can be isolated by a variety of methods known to those skilled in the art. (Ausubel et al., (1987) on "Current Protocols in Molecular Biology", John Wiley and Sons, New York). Such methods include extraction of RNA by differential precipitation (Birnboim, H. C. (1988) *Nucleic Acids Res.*, 16:1487–1497), extraction of RNA by organic solvents (Chomczynski, P. et al. (1987) *Anal. Biochem.*, 162:156–159) and the extraction of RNA with strong denaturants (Chirgwin, J. M. et al. (1979) *Biochemistry*, 18:5294–5299). Poly(A)$^+$ RNA can be selected from whole cell RNA by affinity chromatography on oligo-d(T) columns (Aviv, H. et al. (1972) *Proc. Natl. Acad. Sci.*, 69:1408–1412). Examples of methods for determining cellular messenger mRNA levels for step (c) include, but are not limited to Northern blotting (Alwine, J. C. et al. (1977) *Proc. Natl. Acad. Sci.*, 74:5350–5354), dot and slot hybridization (Kafatos, F. C. et al. (1979) *Nucleic Acids Res.*, 7:1541–1522), filter hybridization (Hollander, M. C. et al. (1990) *Biotechniques*; 9:174–179), RNase protection (Sambrook et. al., (1989) in "Molecular Cloning, A Laboratory Manual", Cold Spring Harbor Press, Plainview, N.Y.), polymerase chain reaction (Watson, J. D. et al. (1992) in "Recombinant DNA" Second Edition, W. H. Freeman and Company, New York) and nuclear run-off assays (Ausubel et. al., (1987) in "Current Protocols in Molecular Biology" Supplement 9 (1990); John Wiley and Sons, New York, N.Y.).

Detection of complexes in Step (b) of the bioassay can also be carried out by a variety of techniques. Detection of the complexes by signal amplification can be achieved by several conventional labelling techniques including radiolabels and enzymes (Sambrook et. al., (1989) in "Molecular Cloning, A Laboratory Manual", Cold Spring Harbor Press, Plainview, N.Y.; Ausubel et al., (1987) in "Current Protocols in Molecular Biology, John Wiley and Sons, New York N.Y.). Radiolabelling kits are also commercially available. The p15 nucleic acid sequence used as a probe in step (a) of the bioassay may be RNA or DNA. Preferred methods of labelling the DNA sequences are with $^{32}$P using Klenow enzyme or polynucleotide kinase. Preferred methods of labeling RNA or riboprobe sequences are with $^{32}$P or $^{35}$S using RNA polymerases. In addition, there are known non-radioactive techniques for signal amplification including methods for attaching chemical moieties to pyrimidine and purine rings (Dale, R. N. K. et al. (1973) *Proc. Natl. Acad. Sci.*, 70:2238–2242; Heck, R. F. (1968) *S. Am. Chem. Soc.*, 90:5518–5523), methods which allow detection by chemiluminescence (Barton, S. K. et al. (1992) *J. Am. Chem. Soc.*, 114:8736–8740) and methods utilizing biotinylated nucleic acid probes (Johnson, T. K. et al. (1983) *Anal. Biochem.*, 133:125–131; Erickson, P. F. et al. (1982) *J. of Immunology Methods*, 51:241–249; Matthaei, F. S. et al (1986) *Anal. Biochem.*, 157:123–128) and methods which allow detection by fluorescence using commercially available products. Non-radioactive labelling kits are also commercially available.

Examples of biological samples that can be used in this bioassay include, but are not limited to, primary mammalian cultures, continuous mammalian cell lines, such as melanocyte cell lines, mammalian organs such as skin or retina, tissues, biopsy specimens, neoplasms, pathology specimens, and necropsy specimens.

In a preferred embodiment, a $^{32}$P radiolabelled p15 probe, as exemplified in Example 1, is used. The approximately 0.9 Kilobase (kb) cDNA (FIG. 1; SEQ ID NO: 1) was cloned into the pCDNA3 vector and the resulting plasmid, deposited with the American Type Culture Collection (ATCC) 12301 Parklawn Drive, Rockville, Md. 20852, USA on Jan. 9, 1995. The full length p15 nucleic acid sequence can be isolated from the pCDNA3 plasmid by digestion with BstXI and NotI restriction enzymes. This 0.9 kb nucleic acid sequence can then be used as a probe. This probe is used to detect p15 mRNA in total RNA or poly A$^+$ RNA isolated from a variety of tissues or biological samples. Alternatively the p15 probe is the 462 base pair BamHI/Pst I fragment from the p15 gene (FIG. 1; SEQ ID NO:1; nucleic acids 15 to 476).

In another embodiment, combinations of oligonucleotide pairs based on the p15 sequence in FIG. 1 (SEQ ID NO:1) are used as Polymerase Chain Reaction (PCR) primers to detect p15 mRNA in a biological sample. These primers can be used in a method following the reverse transcriptase—Polymerase Chain Reaction (RT-PCR) process for amplifying selected RNA nucleic acid sequences as detailed in Ausubel et al., (eds) (1987) In "Current Protocols in Molecular Biology" Chapter 15, John Wiley and Sons, New York, N.Y. The oligonucleotides can be synthesized by automated instruments sold by a variety of manufacturers or can be commercially prepared based upon the nucleic acid sequence of this invention. One skilled in the art will know how to select PCR primers based on the p15 nucleic acid sequence (FIG. 1) for amplifying p15 RNA in a sample. By way of example, oligonucleotide primers designated M2a (5'-CAACAACGACAAGCTCTCCAAGAG-3') (SEQ ID NO:3 FIG. 1; nucleic acids 36 to 58) and M2b (5'GGAACACTGCCGCAAACGTC-3') (SEQ ID NO:4; FIG. 1; nucleic acids 768 to 748) may be used to amplify p15 sequences.

The p15 nucleic acid sequence or portions thereof (FIG. 1: SEQ ID NO:1) of this invention are useful to detect p15 genomic DNA or alterations of the p15 gene in normal or diseased mammalian tissue. By alteration, we mean additions, deletions, substitutions, rearrangements or duplications in the p15 gene sequence or gene amplification of the p15 gene sequence. Therefore, another aspect of the present invention relates to an assay for detecting the p15 genomic DNA or alterations of the p15 gene in a biological sample. Such an assay may comprise the steps of (a) contacting all or part of the nucleic acid sequence of this invention with genomic DNA isolated from a biological sample under conditions allowing a complex to form between said nucleic acid sequence and said genomic DNA, and (b) detecting said complexes. Determining alterations in said p15 gene can be performed by comparison to a control sample or other conventional methods.

Standard methods for isolating DNA from a biological sample, detecting alterations in a gene and detecting complex between the p15 nucleic acid probe and genomic DNA sequences are provided in manuals such as Sambrook et al., (eds) (1989) "Molecular Cloning, A Laboratory Manual", Cold Spring Harbor Press, Plainview, N.Y. and in Ausubel et al., (eds) (1987) in "Current Protocols in Molecular Biology" John Wiley and Sons, New York, N.Y.

All or parts of the p15 nucleic acid sequences of this invention (FIG. 1; SEQ ID NO:1) can also be used as probes to isolate the p15 homologs in other species. In a preferred embodiment the p15 cDNA (FIG. 1; SEQ ID NO:1) is used to screen a mammalian cDNA library; positive clones are selected and sequenced. Examples of tissue sources from which the cDNA library can be synthesized include, but are not limited to skin, retina, melanocytes, neonatal brain, testes and skin. Preferably a melanoma library is screened using the p15 nucleic acid sequences as a probe (FIG. 1; SEQ ID NO:1). One skilled in the art will understand the appropriate hybridization conditions to be used to detect the homologs. Conventional methods for nucleic acid hybridization, construction of libraries and cloning techniques are described in Sambrook et al., (eds) (1989) In "Molecular Cloning A Laboratory Manual" Cold Spring Harbor Press, Plainview, N.Y. and Ausubel et al., (eds) in "Current Protocols in Molecular Biology" (1987), John Wiley and Sons, New York, N.Y.

We have determined that all or parts thereof of the p15 protein is an antigen present on melanoma cells. It is therefore another aspect of this invention to provide p15 nucleic acid probes to be utilized in detecting p15 RNA or alterations in the level of p15 mRNA in biological sample isolated from a mammal afflicted with a disease. Examples of such diseases include, but are not limited to, melanomas. By alterations in the level of p15 mRNA we mean an increase or decrease in the level of an RNA relative to a control sample or the appearance or disappearance of the p15 mRNA relative to a control sample. Detection in the alterations of p15 mRNA may allow for diagnosis or the assessment of the diseased state. Therefore, alterations in the level of p15 mRNA may be predictive of the prognosis for the afflicted mammal.

In another embodiment all or parts thereof of the nucleic acid of this invention can be used in in situ hybridization on mammalian tissues to determine the precise site or subcellular site of expression of the p15 gene within a tissue. A preferred method of labeling the p15 nucleic acid sequence is synthesizing a $^{35}$S-labeled RNA probe by in vitro transcription utilizing polymerases known to those skilled in the art. Conventional methods for preparation of tissues for in situ, synthesis of probes and detection of signal can be found in Ausubel et. al., (eds) (1987) in "Current Protocols in Molecular Biology," John Wiley and Sons, New York, New York Chapter 14 and Vander Ploeg, M., Raap A. K. (1988) In "New Frontiers in Cytology" Goerttler, K., Feichter, GE, Witte. S. (eds) pp 13–21 Springer-Verlag, New York. The probe is then contacted with mammalian tissue sections and in situ analyses performed by conventional methods. Examples of tissues that can be used include, but are not limited to, mammalian embryos, adult mammalian tissues, such as skin, lymph nodes and retina, biopsy specimens, pathology specimens and necropsy specimens. By way of example, p15 in situ probes may be used to evaluate p15 RNA expression in diseased tissue for invasive early melanoma to characterize radial and vertical growth phases of the melanoma lesion and assess the margins of the disease within the tissue known to those skilled in the art.

In yet another embodiment of this invention all or parts thereof of the p15 (SEQ ID NO:1) nucleic acid sequence can be used to generate transgenic animals. Preferably the p15 gene is introduced into an animal or an ancestor of the animal at an embryonic stage, preferably at the one cell stage and generally not later than about the eight cell stage. There are several means by which transgenic animals carrying a p15 gene can be made. One method involves the use of retroviruses carrying all or part of the p15 sequence. The retroviruses containing the transgene are introduced into the embryonic animal by transfection. Another methods involves directly injecting the transgene into the embryo. Yet another methods employs the embryonic stem cell method or homologous recombination method known to workers in the field. Examples of animals into which the p15 transgene can be introduced include, but are not limited to, non-human primates, mice, rats or other rodents. Such transgenic animals may be useful as biological models for the study of melanoma and to evaluate diagnostic or therapeutic methods for melanoma.

This invention further comprises an antibody or antibodies reactive with the p15 protein or peptides having the amino acid sequence defined in FIG. 1 (SEQ ID NO:2) or a unique portion thereof. In this embodiment of the invention the antibodies are monoclonal or polyclonal in origin. p15 protein or peptides used to generate the antibodies may be from natural or recombinant sources or generated by chemical synthesis. Natural p15 proteins can be isolated from mammalian biological samples. Biological samples include, but is not limited to mammalian tissues such as fresh melanoma, skin, retina, primary or continuous cultures of mammalian cells such as melanoma cultures or cultured melanocytes and normal tissues such as fibroblasts. The natural p15 proteins may be isolated by the same methods described above for recombinant proteins. Recombinant p15 proteins or peptides may be produced and purified by conventional methods. Synthetic p15 peptides may be custom ordered or commercially made based on the predicted amino acid sequence of the present invention (FIG. 1; SEQ ID NO:2) or synthesized by methods known to one skilled in the art (Merrifield, R. B. (1963) *J. Amer. Soc.* 85:2149). Examples of p15 peptides include, but are not limited to, AYGLDFYIL (p15 $_{10-18}$; SEQ ID NO:5), and EAYGLDFYIL (p15 $_{9-18}$; SEQ ID NO:6) (peptides are presented in single letter amino acid code). If the peptide is to short to be antigenic it may be conjugated to a carrier molecule to enhance the antigenicity of the peptide. Examples of carrier molecules, include, but are not limited to, human albumin, bovine albumin and keyhole limpet hemo-cyanin ("Basic and Clinical Immunology" (1991) Stites, D. P. and Terr A. I. (eds) Appleton and Lange, Norwalk Conn., San Mateo, Calif.).

Exemplary antibody molecules for use in the detection methods of the present invention are intact immunoglobulin molecules, substantially intact immunoglobulin molecules or those portions of an immunoglobulin molecule that contain the antigen binding site, including those portions of immunoglobulin molecules known in the art as F(ab), F(ab'); F(ab')$_2$ and F(v). Polyclonal or monoclonal antibodies may be produced by methods known in the art. (Kohler and Milstein (1975) *Nature* 256, 495–497; Campbell "Monoclonal Antibody Technology, the Production and Characterization of Rodent and Human Hybridomas" in Burdon et al. (eds.) (1985) "Laboratory Techniques in Biochemistry and Molecular Biology," Volume 13, Elsevier Science Publishers, Amsterdam). The antibodies or antigen binding fragments may also be produced by genetic engineering. The technology for expression of both heavy and light chain genes in *E. coli* is the subject of the PCT patent applications: publication number WO 901443, WO 901443 and WO 9014424 and in Huse et al. (1989) *Science* 246:1275–1281.

The antibodies of this invention may react with native or denatured p15 protein or peptides or analogs thereof. The specific immunoassay in which the antibodies are to be used will dictate which antibodies are desirable. Antibodies may be raised against the p15 protein or portions thereof or against synthetic peptides homologous to the p15 amino acid sequence.

In one embodiment the antibodies of this invention are used in immunoassays to detect the novel p15 protein in biological samples. In this method the antibodies of the present invention are contacted with a biological sample and the formation of a complex between the p15 antigen and antibody is detected. Immunoassays of the present invention may be radioimmunoassay, Western blot assay, immunofluorescent assay, enzyme immunoassay, chemiluminescent assay, immunohistochemical assay and the like. (In "Principles and Practice of Immunoassay" (1991) Christopher P. Price and David J. Neoman (eds), Stockton Press, New York, N.Y.; Ausubel et al. (eds) (1987) in "Current Protocols in Molecular Biology" John Wiley and Sons, New York, N.Y.). Standard techniques known in the art for ELISA are described in *Methods in Immunodiagnosis*, 2nd Edition, Rose and Bigazzi, eds., John Wiley and Sons, New York 1980 and Campbell et al., *Methods of Immunology*, W. A. Benjamin, Inc., 1964, both of which are incorporated herein by reference. Such assays may be direct, indirect, competitive, or noncompetitive immunoassays as described in the art (In "Principles and Practice of Immunoassay" (1991) Christopher P. Price and David J. Neoman (eds), Stockton Pres, NY, N.Y.; Oellirich, M. 1984. *J. Clin. Chem. Clin. Biochem.* 22: 895–904) Biological samples appropriate for such detection assays include mammalian tissues, melanoma and melanocyte cell lines, skin, retina, lymph nodes, pathology specimens, necropsy specimens, and biopsy specimens. Proteins may be isolated from biological samples by conventional methods described in (Ausubel et al., (eds) (1987) in "Current Protocols in Molecular Biology" John Wiley and Sons, New York, N.Y.).

The antibodies of this invention can be used in immunoassays to detect p15 antigen or alteration in the level of expression of the p15 antigen in biological samples isolated from mammals afflicted with a disease or disorder. Examples of biological samples include, but are not limited to, mammalian tissues, biopsy tissue samples, melanoma and lymph node biopsy samples, pathology and tissue samples. Examples of diseases that can be assessed by these immunoassays, include, but are not limited to, melanomas and tissues which are secondary sites for melanoma metastasis. By alteration in level of expression, we mean an increase or decrease of the p15 protein or portions thereof relative to a control sample. Alteration is also meant to encompass substitution, deletion, rearrangement or addition mutants of the p15 protein as well as the presence of the p15 protein or portions thereof in the wrong cellular compartment. Such mutations can be determined by using the antibodies of this invention known to react with specific epitopes of the p15 protein and determining which epitopes are present relative to a control. The antibodies of this invention can therefore be used in an immunoassay to diagnose, assess or prognoses a mammal afflicted with the disease.

In a preferred embodiment, the p15 antibodies of this invention are used to assess the presence of the p15 antigen from a tissue biopsy of a mammal afflicted with melanoma using immunocytochemistry. Such assessment of the delineation of the p15 antigen in a diseased tissue can be used to prognose the progression of the disease in a mammal afflicted with the disease. Specifically the p15 antibodies can be used to characterize the radial and vertical growth phases of the melanoma lesion. Conventional methods for immunohistochemistry are described in (Harlow and Lane (eds) (1988) In "Antibodies A Laboratory Manual", Cold Spring Harbor Press, Cold Spring Harbor, N.Y.; Ausbel et al. (eds) (1987). In Current Protocols In Molecular Biology, John Wiley and Sons (New York, N.Y.).

In another embodiment, antibodies of this invention may be used to purify the p15 protein or portions thereof. Immunoaffinity chromatography can be performed by conventional methods known to one skilled in the art (Ausubel et al. (eds) (1987) in "Current Protocols in Molecular Biology" John Wiley and Sons, New York, N.Y.).

In another embodiment rabbit antisera containing antibodies which specifically recognize the p15 protein is used to detect said protein in Western Blot Analysis. Such antisera is directed to all, or a part or parts of the p15 protein or synthetic peptides derived from the p15 protein sequence. Preferably a p15 synthetic peptide derived from the p15 predicted amino acid sequence is used (FIG. 1; SEQ ID NO:2). The peptide is synthesized by standard methods on an automated peptide synthesizer and purified by high pressure liquid chromatography (HPLC) as described in Example 1. The purified peptide may be conjugated to a carrier as described in (M. Bodanszky (1984) "Principles of Peptide Synthesis," Springer Verlag, New York, N.Y.). Using conventional methods, rabbits may be immunized with the p15 protein or peptide conjugated to carriers. By way of example about 0.1 to 10 (mg) of antigen in adjuvant is used, most preferably about 1 mg of antigen in adjuvant is used. The animal receives similar booster doses and antisera titer is assessed by ELISA assay. Satisfactory levels of antisera are obtained when the anti-peptide antibody titer reaches a plateau. This antibody can be used in the standard immunoassays described above.

The recombinant or natural p15 protein, peptides, or analogs thereof may be used as a vaccine either prophylactically or therapeutically. When provided prophylactically the vaccine is provided in advance of any evidence of melanoma. The prophylactic administration of the p15 vaccine should serve to prevent or attenuate melanoma in a mammal. In a preferred embodiment mammals, preferably human, at high risk for melanoma are prophylactically treated with the vaccines of this invention. Examples of such mammals include, but are not limited to, humans with a family history of melanoma, humans with a history of atypical moles, humans with a history of FAM-M syndrome or humans afflicted with melanoma previously resected and therefore at risk for reoccurrence. When provided therapeutically, the vaccine is provided to enhance the patient's own immune response to the tumor antigen present on the melanoma or metastatic melanoma. The vaccine, which acts as an immunogen, may be a cell, cell lysate from cells transfected with a recombinant expression vector, cell lysates from cells transfected with a p15 recombinant expression vector, or a culture supernatant containing the expressed protein. Alternatively, the immunogen is a partially or substantially purified recombinant p15 protein, peptide or analog thereof. The proteins or peptides may be conjugated with lipoprotein or administered in liposomal form or with adjuvant using conventional methodologies.

While it is possible for the immunogen to be administered in a pure or substantially pure form, it is preferable to present it as a pharmaceutical composition, formulation or preparation.

The formulations of the present invention, both for veterinary and for human use, comprise an immunogen as described above, together with one or more pharmalation ceutically acceptable carriers and, optionally, other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous, intramuscular, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either on their own or as admixtures. These stabilizers are preferably incorporated in an amount of 0.11–10,000 parts by weight per part by weight of immunogen. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating the immunogen of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the p15 protein, peptides and analogs thereof into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

The proteins of the present invention may be supplied in the form of a kit, alone, or in the form of a pharmaceutical composition as described above.

Vaccination can be conducted by conventional methods. For example, the immunogen can be used in a suitable diluent such as saline or water, or complete or incomplete adjuvants. Further, the immunogen may or may not be bound to a carrier to make the protein immunogenic. Examples of such carrier molecules include but are not limited to bovine serum albumin (BSA), keyhole limpet hemocyanin (KLH), tetanus toxoid, and the like. The immunogen also may be coupled with lipoproteins or administered in liposomal form or with adjuvants. The immunogen can be administered by any route appropriate for antibody production such as intravenous, intraperitoneal, intramuscular, subcutaneous, and the like. The immunogen may be administered once or at periodic intervals until a significant titer of anti-p15 immune cells or anti-p15 antibody is produced. The presence of anti-p15 immune cells may be assessed by measuring the frequency of precursor CTL (cytoxic T-lymphocytes) against p15 antigen prior to and after immunization by a CTL precursor analysis assay (Coulie, P. et al., (1992) *International Journal Of Cancer* 50:289–297). The antibody may be detected in the serum using the immunoassay described above.

The administration of the vaccine or immunogen of the present invention may be for either a prophylactic or therapeutic purpose. When provided prophylactically, the immunogen is provided in advance of any evidence or in advance of any symptom due to melanoma. The prophylactic administration of the immunogen serves to prevent or attenuate melanoma in a mammal. When provided therapeutically, the immunogen is provided at (or shortly after) the onset of the disease or at the onset of any symptom of the disease. The therapeutic administration of the immunogen serves to attenuate the disease.

By way of example, a vaccine prepared using recombinant p15 protein or peptide expression vectors may be used. To provide a vaccine to an individual a genetic sequence which encodes for all or part of the p15 nucleic acid sequence is inserted into a expression vector, as described above, and introduced into the mammal to be immunized. Examples of vectors that may be used in the aforementioned vaccines include, but are not limited to, defective retroviral vectors, adenoviral vectors, vaccinia viral vectors, fowl pox viral vectors, or other viral vectors (Mulligan, R. C., (1993) *Science* 260:926–932). The viral vectors carrying all or part of the p15 nucleic sequence can be introduced into a mammal either prior to any evidence of melanoma or to mediate regression of the disease in a mammal afflicted with melanoma. Examples of methods for administering the viral vector into the mammals include, but are not limited to, exposure of cells to the virus ex vivo, or injection of the retrovirus or a producer cell line of the virus into the affected tissue or intravenous administration of the virus. Alternatively the viral vector carrying all or part of the p15 nucleic acid sequence may be administered locally by direct injection into the melanoma lesion or topical application in a pharmaceutically acceptable carrier. By way of example the nucleic acid sequences corresponding to the p15 peptides AYGLDFYIL ($p15_{10-18}$; SEQ ID NO:5) or EAYGLDFYIL ($p15_{9-18}$; SEQ ID NO:6) can be incorporated into the viral vectors. The quantity of viral vector, carrying all or part of the p15 nucleic acid sequence, to be administered is based on the titer of virus particles. By way of example, a range of the immunogen to be administered is $10^6$ to $10^{11}$ virus particles per mammal, preferably a human. After immunization the efficacy of the vaccine can be assessed by production of antibodies or immune cells that recognize the antigen, as assessed by specific lytic activity or specific cytokine production or by tumor regression. One skilled in the art would know the conventional methods to assess the aforementioned parameters. If the mammal to be immunized is already afflicted with melanoma or metastatic melanoma the vaccine can be administered in conjunction with other therapeutic treatments. Examples of other therapeutic treatments includes, but are not limited to, adoptive T cell immunotherapy, coadministration of cytokines or other therapeutic drugs for melanoma.

Alternatively all or parts thereof of a substantially or partially purified the p15 protein may be administered as a vaccine in a pharmaceutically acceptable carrier. By way of example, ranges of p15 protein to be administered may be 0.001 to 100 mg per patient, preferred doses are 0.01 to 100 mg per patient. In a preferred embodiment, the p15 peptides AYGLDFYIL ($p15_{10-18}$; SEQ ID NO:5) or EAYGLDFYIL ($p15_{9-18}$; SEQ ID NO:6) (presented in single letter code) or analogs thereof are administered therapeutically or prophylactically to a mammal in need of such treatment. By way of example, doses may be 0.001 mg to 100 mg, preferred doses are 0.01 mg to 100 mg. The peptide may be synthetically or recombinantly produced. Immunization is repeated as necessary, until a sufficient titer of anti-immunogen antibody or immune cells has been obtained.

In yet another alternative embodiment a viral vector, such as a retroviral vector, can be introduced into mammalian cells. Examples of mammalian cells into which the retroviral vector can be introduced include, but are not limited to, primary mammalian cultures or continuous mammalian cultures, COS cells, NIH3T3, or 293 cells (ATTC #CRL 1573). The means by which the vector carrying the gene may be introduced into a cell includes, but is not limited to, microinjection, electroporation, transfection or transfection using DEAE dextran, lipofection, calcium phosphate or other procedures known to one skilled in the art (Sambrook et al. (eds) (1989) in "Molecular Cloning. A Laboratory Manual", Cold Spring Harbor Press, Plainview, N.Y.). The mammalian cells expressing the p15 antigen can be administered to mammals and serve as a vaccine or immunogen. Examples of how the cells expressing p15 antigens can be administered include, but is not limited to, intravenous, intraperitoneal or intralesional. In a preferred embodiment, the part of the p15 nucleic acid sequence corresponding to the peptide AYGLDFYIL ($p15_{10-18}$; SEQ ID NO:5) and EAYGLDFYIL ($p15_{9-18}$; SEQ ID NO:6) is inserted into the p15 expression vector and introduced into the mammalian cells.

The vaccine formulation of the present invention comprise an immunogen that induces an immune response directed against the melanoma associated antigens such as the melanoma associated p15 antigen. The vaccine formulations may be evaluated first in animal models, or in nonhuman primates and finally in humans. The safety of the immunization procedures is determined by looking for the effect of immunization on the general health of the immunized animal (weight change, fever, appetite behavior etc.) and looking for pathological changes on autopsies. After initial testing in animals, melanoma cancer patients can be tested. Conventional methods would be used to evaluate the immune response of the patient to determine the efficiency of the vaccine.

In yet another embodiment of this invention all, part, or parts of the p15 protein or p15 peptides may be exposed to dendritic cells cultured in vitro. The cultured dendritic cells provide a means of producing T-cell dependent antigens comprised of dendritic cell modified antigen or dendritic cells pulsed with antigen, in which the antigen is processed and expressed on the antigen activated dendritic cell. The p15 antigen activated dendritic cells or processed dendritic cell antigens may be used as immunogens for vaccines or for the treatment of melanoma. The dendritic cells should be exposed to antigen for sufficient time to allow the antigens to be internalized and presented on the dendritic cells surface. The resulting dendritic cells or the dendritic cell process antigens can than be administered to an individual in need of therapy. Such methods are described in Steinman et al. (WO93/208185) and in Banchereau et al. (EPO Application 0563485A1) which are incorporated herein by reference.

In yet another embodiment of this invention T-cells isolated from individuals can be exposed to the p15 protein or portions thereof in vitro and then administered to a patient in need of such treatment in a therapeutically effective amount. Examples of where T-lymphocytes can be isolated, include but are not limited to, peripheral blood cells lymphocytes (PBL), lymph nodes, or tumor infiltrating lymphocytes (TIL). Such lymphocytes can be isolated from the individual to be treated or from a donor by methods known in the art and cultured in vitro (Kawakami, Y. et al. (1989) *J. Immunol.* 142: 2453–3461). Lymphocytes are cultured in media such as RPMI or RPMI 1640 or AIM V for 1–10 weeks. Viability is assessed by trypan blue dye exclusion assay. The lymphocytes are exposed to all or part of the p15 protein for part or all of the culture duration. In a preferred embodiment the lymphocytes are exposed to the AYGLD-FYIL ($p15_{10-18}$; SEQ ID NO:5) peptide or EAYGLDFYIL ($p15_{9-18}$; SEQ ID NO:6) (presented in single letter code). By way of example, a concentration of 1–10 micrograms(ug)/ml peptides per $10^7$ cells for all or part of the duration of lymphocyte culture may be used. After being sensitized to the peptide the T-lymphocytes are administered to the mammal in need of such treatment. Examples of how these sensitized T-cells can be administered to the mammal include but are not limited to, intravenously, intraperitoneally or intralesionally. Parameters that may be assessed to determine the efficacy of these sensitized T-lymphocytes include, but are not limited to, production of immune cells in the mammal being treated or tumor regression. Conventional methods are used to assess these parameters. Such treatment can be given in conjunction with cytokines or gene modified cells (Rosenberg, S. A. et al. (1992) *Human Gene Therapy*, 3: 75–90; Rosenberg, S. A. et al. (1992) *Human Gene Therapy*, 3: 57–73).

In addition to use as a vaccine, the compositions can be used to prepare antibodies to p15 antigen, peptides or analogs thereof. The antibodies can be used directly as anti-melanoma agents. To prepare antibodies, a host animal is immunized using the p15 protein, peptides or analogs thereof as the immunogen and bound to a carrier as described above for vaccines. The host serum or plasma is collected following an appropriate time interval to provide a composition comprising antibodies reactive with the immunogen. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-cancer agents such as chemotherapy.

The antibody compositions can be made even more compatible with the host system by minimizing potential adverse immune system responses. This is accomplished by removing all or a portion of the Fc portion of a foreign species antibody or using an antibody of the same species as the host animal, for example, the use of antibodies from human/human hybridomas. Humanized antibodies (i.e., nonimmunogenic in a human) may be produced, for example, by replacing an immunogenic portion of an antibody with a corresponding, but nonimmunogenic portion (i.e., chimeric antibodies). Such chimeric antibodies may contain the reactive or antigen binding portion of an antibody from one species and the Fc portion of an antibody (nonimmunogenic) from a different species. Examples of chimeric antibodies, include but are not limited to, non-human mammal-human chimeras, rodent-human chimeras, murine-human and rat-human chimeras (Robinson et al., International Patent Application 184,187; Taniguchi M., European Patent Application 171,496; Morrison et al., European Patent Application 173,494; Neuberger et al., PCT Application WO 86/01533; Cabilly et al., 1987 Proc. Natl. Acad. Sci. USA 84:3439; Nishimura et al., 1987 Canc. Res. 47:999; Wood et al., 1985 Nature 314:446; Shaw et al., 1988 J. Natl. Cancer Inst. 80: 15553, all incorporated herein by reference).

General reviews of "humanized" chimeric antibodies are provided by Morrison S., 1985 Science 229:1202 and by Oi et al., 1986 BioTechniques 4:214.

Suitable "humanized" antibodies can be alternatively produced by CDR or CEA substitution (Jones et al., 1986 Nature 321:552; Verhoeyan et al., 1988 Science 239:1534; Biedleret al. 1988 J. Immunol. 141:4053, all incorporated herein by reference).

The antibodies or antigen binding fragments may also be produced by genetic engineering. The technology for expression of both heavy and light chain genes in *E. coli* is the subject the PCT patent applications; publication number WO 901443, and WO 9014424 and in Huse et al., 1989 Science 246:1275–1281.

The antibodies can also be used as a means of enhancing the immune response. The antibodies can be administered in amounts similar to those used for other therapeutic administrations of antibody. For example, pooled gamma globulin is administered at a range of about 1–100 mg per patient. Thus, antibodies reactive with the p15 antigen can be passively administered alone or in conjunction with other anti-cancer therapies to a mammal afflicted with melanoma. Examples of anti-cancer therapies include, but are not limited to, chemotherapy, radiation therapy, adoptive immunotherapy therapy with TIL.

Alternatively, anti p15 antigen antibodies can be induced by administering anti-idiotype antibodies as immunogens. Conveniently, a purified anti-p15 antibody preparation prepared as described above is used to induce anti-idiotype antibody in a host animal. The composition is administered to the host animal in a suitable diluent. Following administration, usually repeated administration, the host produces anti-idiotype antibody. To eliminate an immunogenic response to the Fc region, antibodies produced by the same species as the host animal can be used or the Fc region of the administered antibodies can be removed. Following induction of anti-idiotype antibody in the host animal, serum or plasma is removed to provide an antibody composition. The composition can be purified as described above for anti-p15 antibodies, or by affinity chromatography using anti-p15 antibodies bound to the affinity matrix. The anti-idiotype antibodies produced are similar in conformation to the authentic p15-antigen and may be used to prepare an p15 melanoma antigen vaccine rather than using the p15 protein, peptides analogs or portions thereof.

When used as a means of inducing anti-p15 antibodies in an animal, the manner of injecting the antibody is the same as for vaccination purposes, namely intramuscularly, intraperitoneally, subcutaneously, interlesionally, or the like in an effective concentration in a physiologically suitable diluent with or without adjuvant. One or more booster injections may be desirable.

The p15 derived proteins or peptides of the invention are also intended for use in producing antiserum designed for pre- or post-disease prophylaxis. Here the p15 antigen, peptides or analogs thereof is formulated with a suitable adjuvant and administered by injection to human volunteers, according to known methods for producing human antisera. Antibody response to the injected proteins is monitored, during a several-week period following immunization, by periodic serum sampling to detect the presence of anti-p15 serum antibodies, using an immunoassay as described herein.

The antiserum from immunized individuals may be administered as a prophylactic measure for individuals who are at risk of developing melanoma. The antiserum is also useful in treating an individual afflicted with melanoma for post-disease prophylaxis.

For both in vivo use of antibodies to p15 antigen and anti-idiotype antibodies and diagnostic use, it may be preferable to use monoclonal antibodies. Monoclonal anti-p15 antibodies or anti-idiotype antibodies can be produced as follows. The spleen or lymphocytes from an immunized animal are removed and immortalized or used to prepare hybridomas by methods known to those skilled in the art. (Goding, J. W. 1983. Monoclonal Antibodies: Principles and Practice, Pladermic Press, Inc., NY, N.Y., pp. 56–97). To produce a human-human hybridoma, a human lymphocyte donor is selected. A donor known to have a melanoma carrying the p15 antigen may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies. Examples of p15 peptides include, but not limited to, AYGLDFYIL (p15$_{10-18}$; SEQ ID NO:5) and EAYGLDFYIL (p15$_{9-18}$; SEQ ID NO:6) (peptides are presented in single letter amino acid code).

Antibodies secreted by the immortalized cells are screened to determine the clones that secrete antibodies of the desired specificity. For monoclonal p15 antigen or peptide antibodies, the antibodies must bind to p15 antigen or peptide. For monoclonal anti-idiotype antibodies, the antibodies must bind to anti-p15 antibodies. Cells producing antibodies of the desired specificity are selected.

The antibodies or chimeric antibodies described herein may also be coupled to toxin molecules radioisotopes and drugs by conventional methods (Vitetta et al. (1991) in "Biologic Therapy of Cancer" De Vita VT, Hellman S., Rosenberg, S. A. (eds) J. B. Lippincott Co. Philadelphia; Larson, S. M. et al. (1991) in "Biological Therapy of Cancer" De Vita V. T., Hellman S., Rosenberg, S. A. (eds) J.B. Lippincott Co., Philadelphia). Examples of toxins to which the antibodies may be coupled to include, but are not limited to, ricin or diphtheria toxin. Examples of drugs or chemotherapeutic agents include, but are not limited to, cyclophosphamide or doxorubcin. Examples of radioisotopes, include, but are not limited to, $^{131}$I. Antibodies covalently conjugated to the aforementioned agents can be used in cancer immunotherapy for treating melanoma.

Local administration to the afflicted site may be accomplished through means known in the art, including, but not limited to, topical application, injection, and implantation of a porous device containing cells recombinantly expressing the infusion, implantation of a porous device in which the p15 antibodies or chimeric antibodies, antibodies coupled to toxins, drugs or radiolabels or portions thereof are contained.

The above described antibodies and antigen binding fragments thereof may be supplied in kit form alone, or as a pharmaceutical composition for in vivo use. The antibodies may be used for therapeutic uses, diagnostic use in immunoassays or as an immunoaffinity agent to purify the p15 protein or peptides as described herein.

The present invention also provides a tyrosinase nucleic acid sequence and amino acid sequence (FIGS. 7A–7D; SEQ ID NOS. 9 and 10) and antigenic or immunogenic peptides derived from the tyrosinase protein sequence. The tyrosinase nucleic acid sequence reported herein (FIGS. 7A–7D; SEQ ID NO. 9) differs from the previously reported sequence for tyrosinase (Bouchard, et al. (1989) J. Exp. Med. 169:2029–2042) in that nucleotide 94 was changed from A to T, resulting in the substitution of an S (single letter code) residue for an R (single letter code) amino acid residue. This variation has not been observed in other tyrosinase alleles or mutations (Spritz, R. A. (1993) Sem. Dermatol, 12:167–172; Oetting, W. S. et al (1993), Hum Mutat 2:1–6, Tripathi, R. K., et al. (1992) Am. J. Med Genet. 43:865–871).

The immunogenic peptides derived from the tyrosinase sequence (FIGS. 7A–7D) represent antigenic portions of the tyrosinase protein (FIG. 5) recognized by HLA-A24 restricted TIL. Examples of immunogenic peptides include, but are not limited to, AFLPWHRLF (SEQ ID NO:7) and overlapping peptide AFLPWHRLFL (SEQ ID NO:8). This invention further includes analogs of these immunogenic peptides derived from the tyrosinase amino acid sequence. The term analog includes any peptide which displays the functional aspects of these immunogenic peptides. The term analog also includes conservative substitution or chemical derivative of the peptides as described above. These immunogenic peptides may be synthetically or recombinantly produced in the same manner or fashion as described above for p15.

In another embodiment the immunogenic peptides (SEQ ID NO:7 and 8) derived from the tyrosinase amino acid sequence may be used as a vaccine either therapeutically or prophylactically. When provided, prophylactically the vaccine is provided in advance of any evidence of melanoma. The prophylactic administration of these peptides should serve to prevent or attenuate melanoma in a mammal.

In a one embodiment, mammals preferably humans, at high risk for melanoma are prophylactically treated with these vaccines. Alternatively, the vaccine may be provided therapeutically to enhance the patients own immune response to the tumor antigen prescribed on the melanoma or metastatic melanoma. The vaccine, which acts as an immunogen, may be a cell, cell lysate from cells transfected with a recombinant expression vector carrying a nucleic acid sequences encoding tyrosinase immunogenic peptide or a culture supernatant containing the expressed protein. Expression vectors into which nucleic acid sequences encoding these immunogenic peptides may be introduced are the same as those described above for p15. Alternatively, the immunogen is a partially or substantially purified recombinant tyrosinase peptide or analog thereof.

While it is possible for the immunogen to be administered in a pure or substantially pure form, it is preferable to present it as pharmaceutical compositions, formulations or preparations as described above for p15. Vaccination can be conducted by conventional methods previously described above for p15.

The tyrosinase immunogenic peptides and nucleic acids sequences encoding them may be used in bioassays, or to generate antibodies in the same manner or fashion as described above for p15.

In yet another embodiment of this invention, multivalent vaccines against one or more melanoma antigens are provided. Such multivalent vaccines may comprise all or part of the p15 protein or peptides or tyrosinase peptides disclosed herein or combinations thereof. Alternatively, multivalent vaccines comprising p15 protein or peptides or the immunogenic tyrosinase peptides disclosed herein may be combined with other known melanoma antigens to create a multivalent melanoma vaccine. Examples of known melanoma antigens include, but are not limited to, MART-1, gp100 MAGE-1 and MAGE-2.

Once the genes or nucleic acid sequences encoding melanoma antigens are identified, the next step is to determine the antigenic portion or epitope of the protein encoded by these genes. Therefore, in yet another embodiment of this invention, a method is provided for assessing the immunogenicity of peptides derived from the predicted amino acid sequences of the p15 protein (FIG. 1; SEQ ID NO:2). The method comprises the steps of: (a) preparing a plurality of peptides based on the p15 (FIG. 1; SEQ ID NO:2) amino acid sequence; (b) incubating at least one of said peptides with a mammalian cell line; (c) exposing said mammalian cells incubated with said peptide to tumor infiltrating lymphocytes (TIL); and (d) screening for recognition of TIL with said cells incubated with said peptide. It is preferred that peptides of about 25 to 5 amino acids be used, more preferably 20 to 10 amino acids and most preferably 9–10 amino acids. Examples of cells that may be used in step (b) include, but are not limited to, T2 cells, (Cerundolo, V. et al. (1990) Nature, 345: 449–452) or EBV transformed B cell lines (Topalian et al. (1989) J. Immunol. 142: 3714–3725). Examples of how to assess recognition of the cells incubated with peptide include but is not limited to, $^{51}CR$ release cytotoxicity assay (Cerundolo, V. et al. (1990) Nature 345:449–452.) or lymphokine assays such as γ-IFN, GM-CSF or TNF secretion. (Schwartzentruber, D. et al., (1991) J. of Immunology 146:3674–3681).

T cells recognize antigen complexed with MHC Class 1 molecules. The MHC locus in all mammalian species contains numerous genes and is highly polymorphic. Different MHC molecules or haplotypes types bind different antigens. In humans the HLA complex contains the HLA-A, HLA-B and HLA-C gene loci which encode class I molecules. Lymphocytes will recognize tumor antigens on the context of HLA Class 1 molecule. If the cells containing the recombinant p15 expression vector are to be screened by the TIL but are not human cells, such as COS cells, or do not express a desired haplotype an expression vector containing an MHC Class I gene may also be introduced into the cells. This, represents yet another alternative embodiment of the invention. Cells expressing p15 or tyrosinase antigens and HLA antigens can be screened with TIL to detect the presence of tumor antigens in the context of a specific MHC Class 1 restriction type. The appropriate haplotype is determined by the haplotype of the tumor from which the library is derived. Examples of MHC Class I genes that may be used include, but are not limited to, HLA-A, HLA-B and HLA-C genes. Examples of preferred MHC specificities or restriction types include, but is not limited to HLA-A1, HLA-A2, such as the HLA-A2.1 subtype, or HLA-A24 (Zemmour, J. et al. (1992) Tissue Antigens 40:221–228).

All books, articles, and patents referenced herein are incorporated by reference. The following examples illustrate various aspects of the invention and in no way intended to limit the scope thereof.

EXAMPLE 1

Cloning Of The p15 Gene Recognized By Melanoma Specific HLA-A24 Restricted Tumor Infiltrating Lymphocytes Materials and Methods Cell lines Melanoma-specific CTL were grown and expanded from TIL in media containing 6000 IU of IL2 (Cetus-Oncogen Division, Chirion Corp, Emeryville, Calif.) as described in Rosenberg, S. A., et al., (1988). N Endl J Med 319:1676. Briefly, tumors were finely minced and digested with a mixture of collagenase, hyaluronidase and DNase overnight. The resulting single cell suspensions were placed in a single step gradient to remove non-viable cells and red blood cells, and the interface containing viable cells collected. The mixture of tumor and mononuclear cells were cultured at 2.5–5×10$^5$ cells/mL in RPMI media containing 6000 IU/ml of IL2, 10% pooled human AB (BioWhittaker, Walkersville, Md.) serum. In addition, condition medium from a 4 day culture of allogeneic lymphokine activated killer cells was added at a final concentration of 20%. Under these condition, selective growth of pure lymphocytes were established, and cells were assayed between 45 and 70 days of culture. Melanoma cell lines 888, 1290, 928, 1300, 397 and 624 were established in our laboratory (Topalian, S. L., et al. (1990) J. Immunol 144:4487–4495), the 293 human kidney cell line obtained from Dr. Joel Jesse (Life Technologies, Inc., Gaithersburg, Md.), and COS-7 cells obtained from W. Leonard (National Institutes of Health). The melanocyte cell lines NEHM680, expressing HLA-A29,A31,B44, and B60, and NEHM2488, expressing HLA-A2,A24,B35, and B39 were obtained from Clonetics (San Diego, Calif.).

cDNA Library Construction and Screening

Construction and screening of a cDNA library prepared from melanoma 888 was carried out as previously described (Robbins, P. F., et al. (1994) *Cancer Research* 54:3124). Briefly, cDNA was synthesized using reverse transcriptase and an oligo-dT Not I primer adaptor using the Promega Riboclone cDNA synthesis system (Promega, Madison, Wis.). Following the addition of BstXI linkers (InVitrogen, San Diego, Calif.), the cDNA was digested with Not I, and the cDNA was ligated to pCDNA3. The DNA was transformed into Max Efficiency DH5a cells (Life Technologies, Gaithersburg, Md.), and 50–100 bacterial colonies were pooled and grown in media for 4–6 hour. DNA was purified from bacteria using the QIA prep 8 plasmid kit (Qiagen, Chatsworth, Calif.). Transient transfections of the cDNA pools were carried out using stable transfectants of 293 cells expressing HLA-A24 (293-A24). The 293 cells were transfected with a HLA-A24 (Zemmour, J, et al. (1992) *Tissue Antigens*, 40:221–228) gene isolated from 888 mel cells by RT-PCR. The HLA-24 gene was cloned into pCDNA3, and a stable cell line selected. The 293-A24 cells ($10^5$) were transfected for 18–24 hours with pools containing between 50 and 100 cDNAs, $1 \times 10^5$ TIL were incubated with transfectants for 18–24 hours, and GM-CSF release measured.

Northern Blot Analysis

Total RNA was isolated by the guanidium isothiocyanate/cesium chloride method. Total RNA from human normal tissue was purchased from Clontech (Palo Alto, Calif.). 20 ug of total RNA was subject to electrophoresis on a 1% agarose formaldehyde gel, and transferred to a nylon membrane. The membrane was pre-hybridized with QuickHyb (Stratagene), and hybridized with a 462 bp BamHI/PstI fragment (FIG. 1; nucleotides 15-476) from the p15 CDNA was labelled with $^{32}$P using the standard random primer method. Hybridization was carried out with QuickHyb according to the manufacturer's instructions, and the membrane was washed with 0.1×SSC at 55° C. for 30 minutes (min) before autoradiography.

Sequencing and PCR Analysis

DNA sequencing was carried out using a Sequenase 2.0 kit (USB, Cleveland, Ohio). Database searches with the nucleotide and deduced amino acid sequences were carried out using Blast and Fasta sequence alignment algorithms (Program Manual for the Wisconsin Package, Version 8, September 1994, Genetics Computer Group, 575 Science Drive, Madison, Wis., USA 53711). Total cellular RNA was isolated by the guanidinium isothiocyanate/cesium chloride centrifugation method. A 2 μg sample of RNA brought up to 20 μl in first strand synthesis buffer containing 0.5 μg of oligo(dT), 0.5 mM dNTP, 10 mM DTT, and 200 U of Superscript reverse transcriptase (BRL, Gaithersburg, Md.). Following incubation at 42° Centigrade (C) for 50 min, a PCR was carried out with 1 μl of the RT reaction using primers M2a (5'- CAACAACGACAAGCTCTCCAAGAG-3') (SEQ ID NO:3) and M2b (5'-GGAACACTGCCGCAAACGTC-3') (SEQ ID NO:4) located in the 5' and 3' untranslated regions, respectively. The PCRs were carried out by heating reactions to 94° C. for 5 min, followed by 30 cycles of amplification at 94° C. for 30 sec., annealing at 55° C. for 30 sec., and extension at 72° C. for 1 min. The PCR products were purified by agarose gel electrophoresis, modified using the Prime PCR cloner (5prime-3prime, Boulder, Colo.), and cloned into EcoRV-digested pCDNA3 (INVITROGEN, San Diego, Calif.).

Peptide Synthesis and Analysis

Peptides were made on a Gilson AMS 422 Multiple Peptide Synthesizer using standard Fmoc chemistry. Peptides were purified on an R2 reverse phase HPLC column (PerSeptive Biosystems) using an 1% to 60% acetonitrile gradient in water containing 0.05% TFA, and were >95% pure.

A TIL line grown from patient 888 in 1990, TIL 888, was previously shown to recognize melanoma in an HLA-A24 restricted manner (Schwartzentruber, D. J., et al., (1991). *J. Immunol.* 146:3674), and the gene encoding an antigen recognized by TIL 888, tyrosinase, was cloned from a melanoma cell cDNA library (Robbins, P. F., et al. (1994). *Cancer Research* 54:3124; FIGS. 7A–7D). Infusion of TIL 888 into patient MG resulted in complete regression of multiple metastases. However, three years later a recurrent pelvic tumor was removed from this patient, and a second TIL line, TIL 1290, was established from this tumor. A cytotoxicity assay carried out with TIL 1290 demonstrated that the majority of melanomas which express HLA-A24 were lysed (Table 1). Fresh, uncultured melanoma cells from the autologous patient (1290 fresh melanoma), as well as another uncultured HLA-A24 melanoma were lysed by TIL 1290, whereas two non-A24 expressing melanomas 397 TC and 624TC, 888 EBV B cells established from patient MG, Daudi (B lymphoblast cell line, American Type Culture Collection, Rockville, MD, ATCC #CCL213) and K562 (chronic myelogenous leukemia cell line American Type Culture Collection, ATTC #CCL243) cells were not lysed. These results indicate that TIL 1290, like TIL 888, predominantly recognizes one or more shared melanoma antigens in the context of HLA-A24.

The specificity of TIL 1290 and TIL 888 was then examined in a cytokine release assay (Table 2). The results indicated that both 888 and 1290 mel strongly stimulate TIL 888 and TIL 1290. Two other HLA-A24 expressing melanocytes, 928 and 1300 mel, stimulated strong cytokine release from TIL 1290 and 888, whereas two melanomas which did not express HLA-A24, 397, and 624, did not stimulate significant cytokine release from these TIL. A stable transfectant of 397 mel expressing HLA-A24 stimulated significant cytokine release from both 888 and 1290 TIL, demonstrating the restriction of the cell line. The recognition pattern of TIL 888 and 1290 was not identical, however, since an HLA-A24 expressing melanocyte line, NEHM2488, stimulated the release of low but significantly levels of GM-CSF from TIL 888 (160 pg/ml), but not TIL 1290.

The TIL 1290 line as then examined for recognition of tyrosinase, as well as MART-1 and gp100, two antigens which have recently shown to be recognized by HLA-A2 restricted melanoma-specific T cells (Kawakami, Y., S. et al., (1994). *Proc. Natl. Acad. Sci.* 91:6458–6462; Kawakami, Y., S. et al., (1994). *Proc. Natl. Acad. Sci.* U.S.A. 91:3515). In addition, the melanocyte lineage protein gp75 was tested for recognition by TIL 1290, since results have demonstrated that this glycoprotein is recognized by an HLA-A31 restricted TIL. TIL 888 was strongly stimulated by COS cells transiently transfected with tyrosinase plus HLAA-A24 but not MART-1, gp100 or gp75, whereas transfectants of tyrosinase, as well as MART-1, gp100, or gp75 failed to stimulate TIL 1290 (Table 2) Transfectants of COS expressing MART-1 plus HLA-A2 stimulated TIL 1235 and transfectants expressing gp100 plus HLA-A2 stimulated TIL 1200 (Table 2), as previously reported (Kawakami, Y., S. et al., (1994). *Proc. Natl. Asad. Sci.* U.S.A. in press; Kawakami, Y., S. et al., (1994), *Proc. Natl. Acad. Sci.* U.S.A. 91:3515). In addition, transfectants expressing gp75 plus HLA-A31 stimulated TIL 586. These results indicated that TIL 1290 recognized a previously undescribed melanoma antigen.

In order to isolate the gene encoding this antigen, pools of clones prepared from an 888 melanoma cDNA library (Robbins, P. F., et al. (1994). *Cancer Research* 54:3124) were transiently transfected into 293 cells which expressed HLA-A24 (293-A24) and assayed for their ability to stimulate GM-CSF release from TIL 1290. Transfections were carried out with 176 cDNA pools containing between 50 and 100 cDNAs. Transfectants of all but three of the pools stimulated the release of less than 8 pg/ml of GM-CSF from TIL 1290, which was the limit of sensitivity for the cytokine assay. Transfectants of the three positive pools stimulation the release of 17, 28 and 11 pg/ml of GM-CSF from TIL 1290, but on repeated assay only the third positive pool was found to reproducibly stimulate significant cytokine release from TIL 1290. Positive sub-clones were isolated from this pool, and a single cDNA was isolated which strongly stimulated TIL 1290 but not TIL 888 upon transfection of 293-A24 cells (Table 3).

This cDNA clone was sequenced and found to represent a gene not previously reported. (FIG. 1). The only long open reading frame in this clone encoded a 128 amino acid polypeptide with a MW of about 15 kD beginning with the first in frame methionine. This gene did not appear to contain any features which would identify it as a member of any known gene family, and lacked a conventional leader sequence, as well as consensus sites for N-linked glycosylation and any extended hydrophobic domains. The gene's product therefore appears to represent a small cytoplasmic or nuclear protein of unknown function, and was designated p15.

Northern blot analysis was then carried out to determine the pattern of expression of this gene (FIG. 2). These results indicated that a variety of normal tissues expressed comparable message levels to those found in melanoma cells. The normal tissues examined included spleen, testes, thymus, liver, kidney, brain, adrenal, lung, and retinal tissue, as well as EBV B cells isolated from patient 888. The lower level of expression found in EBV B cells appeared to be due to under-loading of this sample, since a subsequent blot demonstrated that relatively similar amounts of p15 message were expressed in 1290 melanoma and EBV B cells, as well as fibroblasts isolated from patient 888.

To determine if the epitope recognized by TIL 1290 resulted from a mutation of the p15 gene product, RT-PCR was used to isolate gene products expressed in 888 EBV B cells. The sequence of one of the products isolated by RT-PCR from EBV B RNA, Clone 1, was identical to the p15 sequence in the region sequenced (FIG. 3), and appears to represent a full length clone. Three out of the nine clones isolated by RT-PCR from EBV B cells appeared to contain truncated inserts. The sequence of one of the truncated clones, Clone 2, appears to have resulted from a recombination between residues 199 and 738 of the p15 gene (FIG. 3). Clone 2 also contained one nucleotide difference from the sequence of p15 at codon 8, resulting in substitution of asparagine for aspartic acid.

Expression of the epitope recognized by TIL 1290 was then tested by transfection of the full length and truncated genes (clones 1 and 2 respectively) isolated from 888 EBV B cells. Transfection of 293-A24 cells with either construct (clone 1 or 2) was found to confer the ability to stimulate levels of cytokine release comparable to that stimulated by the original p15 cDNA clone (Table 4). This data indicated that the gene encoding this antigen was also expressed in the patient's B cells.

Figure 4:
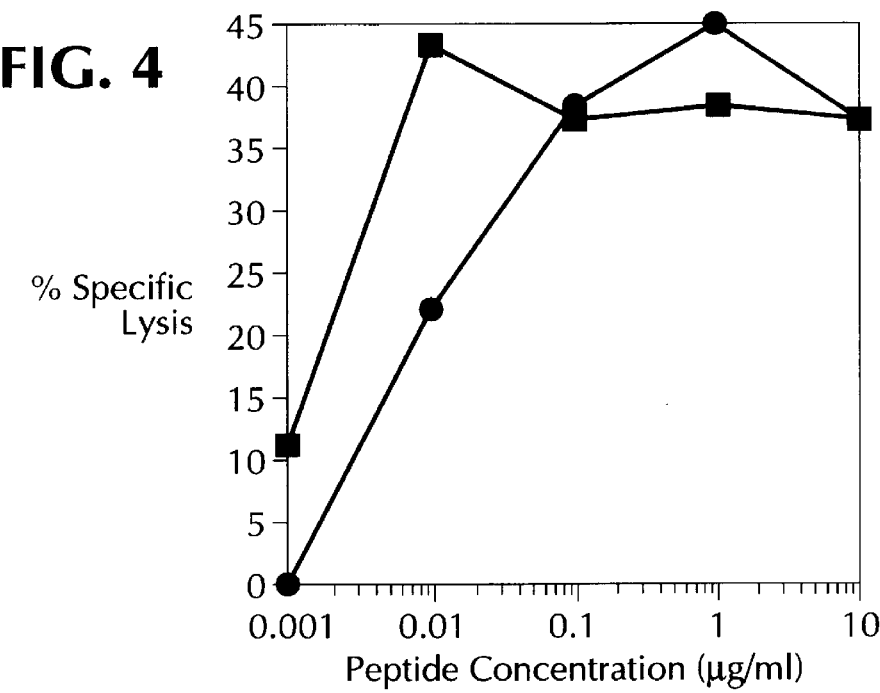
FIG. 4 shows titration of p15 peptides. The peptides $p15_{10-18}$ -■- and $p15_{9-18}$ -•-were incubated with 888 EBV B cells at the indicated concentrations for two hours before incubation with TIL 1290 in a 4 hour $^{51}$Cr release assay at an Effector (E): Target (T) ratio of 40:1.

The sequence of Clone 2, which was recognized by TIL 1290, contained only 18 amino acids of the deduced coding region identified in the p15 sequence. A motif has recently been defined for HLA-A24-binding peptides by isolating peptides from this HLA restriction element, as well as by substituting amino acids at the anchor residue positions in synthetic peptides (Kubo, R. T. et al. (1994) *J. Immunol* 152:3913). This motif consisted of an aromatic residue or methionine at position two and either phenylalanine, leucine, isoleucine or tryptophan at the last position. A single peptide 9-mer within the first 18 amino acids of the p15 protein, AYGLDFYIL ($p15_{10-18}$; SEQ ID NO:5), conformed to this motif. This peptide, along with the overlapping 10-mer EAYGLDFYIL ($p15_{9-18}$; SEQ ID NO:6), were then synthesized and tested for their ability to sensitize 888 EBV B cells for lysis by TIL 1290 (FIG. 4) in a $^{51}$Cr release assay (Kawakami, et al. (1988) *J. Exp. Med.*, 168:2183–2191) and stimulate cytokine release from TIL 1290 (Table 5). The $p15_{10-18}$ peptide was capable of sensitizing cells for lysis at a minimum concentration of 1 ng/ml, and 10ng/ml of the $p15_{9-18}$ peptide was required for sensitization. Incubation of 888 EBV B cells with both peptides was found to be capable of stimulating significant GM-CSF release from TIL 1290 at a minimum concentration of 10 ng/ml.

To isolate additional antigens recognized by TIL 1290, screening of an additional 700 pools, containing approximately 35,000 cDNA clones was performed. A second cDNA clone was isolated which strongly stimulated TIL 1290. Partial sequencing of this clone revealed that it represented a transcript of the p15 gene, lacking only 8 base pairs from the end of the 5' untranslated region of p15. P15 may represent the predominant product recognized by TIL 1290.

The gene encoding the antigen recognized by TIL 1290, p15, does not possess significant similarities to known genes. TIL 1290 failed to recognize autologous EBV B cells which had not been pulsed with peptides, and normal fibroblasts but recognized a specific melanoma antigen in the context of HLA-A24. Northern blots showed that normal tissues, including EBV B cells (FIG. 2) and fibroblasts, contained significant levels of RNA encoding this protein (FIG. 2). The gene encoding the p15 protein could also be isolated from EBV B cells and could confer reactivity of TIL 1290 to 293-A24 cells, suggesting that this represents a non-mutated normal gene.

Patient 888 was found to have malignant melanoma, and TIL and melanoma lines, designated 888, were established in 1989. The TIL 888 was infused into the autologous patient along with IL2, and a complete remission of subcutaneous , mucosal, and lung metastases was observed (Rosenberg, S. A., et al., (1990). *N. Enql. J. Med.* 323:570). Use of TIL 888 to screen a CDNA library prepared from 888 mel resulted in the cloning of the tyrosinase gene (Robbins, P. F., et al. (1994). *Cancer Research* 54:3124), a gene also shown to be recognized by HLA-A2 restricted CTL (Brichard, V., et al., (1993). *J Exp. Med.* 178:489). The dramatic response to therapy following infusion of TIL 888 into patient MG suggest that this may be an important tumor rejection antigen for HLA-A24 patients. A pelvic tumor recurred in patient 888 three years after treatment and was resected. This tumor, 1290 mel, did not to represent an antigen loss variant of tyrosinase, since 888 TIL responded strongly to this tumor. Since the factors responsible for tumor recurrence were unknown, a mixture of TIL 1290, derived from the recurrence, and TIL 888 were infused into patient 888. This treatment resulted in complete tumor regression of recurrent pelvic cancer, and this patient remains disease free two years after this therapy. Thus, the antigen recognized by TIL 1290 may also represent a cancer regression antigen important for therapy.

All of the tumor antigens which have so far been described in melanoma appear to represent the products of non-mutated genes expressed in normal tissues. The proteins MART-1 and gp100, gp75 and tyrosinase are expressed in normal cultured melanocytes and are expressed in retina as well as normal skin melanocytes in vivo. Gp75 and tyrosinase have been shown to be involved in melanin synthesis.

TABLE 1

Specificity of Lysis by TIL 1290

| TARGET | HLA-A24 expression | % LYSIS[a] 40:1 | 10:1 |
|---|---|---|---|
| 1290 TC[b] | + | 65 | 59 |
| 888 TC | + | 68 | 70 |
| 1300 TC | + | 47 | 34 |
| 928 TC | + | 30 | 28 |
| 938 TC | + | 59 | 42 |
| 1102 TC | + | 11 | 11 |
| 1123 TC | + | 9 | 5.0 |
| 1195 TC | + | 11 | 4.0 |
| 501 TC | + | 5 | 2.0 |
| 1290 fresh mel[c] | + | 19 | 28 |
| 1406 fresh mel | + | 24 | 12 |
| 397-A24 | + | 20 | 14 |
| 397 TC | − | 2 | 2 |
| 624 TC | − | 3 | 2 |
| 888 EBV | + | −3 | −1 |
| 501 EBV | + | 3 | 3 |
| K562 | − | 2 | −1 |
| Daudi | − | −2 | −6 |

[a]% lysis by TIL 1290 at the indicated effector (E):(T) target ratio. All targets were lysed greater than 15% by lymphokine activated killer cells at an E:T ratio of 40:1.
[b]TC mel, tissue culture melanoma cell line.
[c]Fresh mel, cryopreserved, noncultured melanoma cells.

TABLE 2

Specificity of cytokine release from TIL 1290

| STIMULATOR | | GM-CSF (pg/ml) TIL[a] | |
|---|---|---|---|
| Cell line | Transfected genes | 1290 | 888 |
| COS-7 | pCDNA3[b] | 10 | 120 |
| COS-7 | pCDNA3 + HLA-A24 | 10 | 80 |
| COS-7 | pCDNA3 + tyrosinase | 10 | 130 |
| COS-7 | tyrosinase + HLA-A24 | 20 | 1500 |
| COS-7 | MART-1[c] + HLA-A24 | 20 | 140 |
| COS-7 | gp100[c] + HLA-A24 | 10 | 120 |
| COS-7 | gp75[c] + HLA-A24 | 20 | 130 |
| 888 mel | None | 1500 | 3200 |
| 1290 mel | None | 500 | 800 |
| 928 mel | None | 10 | 490 |
| 1300 mel | None | 120 | 1900 |
| 397 mel | None | <8 | <8 |
| 397-A24 mel | None | 110 | 540 |
| 624 mel | None | <8 | <8 |
| NEHM2488[d] | None | 10 | 160 |
| NEHM680 | None | <8 | <8 |
| None | Nane | <8 | <8 |

[a]10⁵ of the indicated TIL were incubated with the stimulators for 18 hours and GM-CSF release
[b]COS-7 cells (5 × 10⁴) were transfected with 200 ng of plasmid DNA containing the indicated tumor antigen genes or vector control with 50 ng of plasmid DNA containing the appropriate restriction element.

TABLE 2-continued

Specificity of cytokine release from TIL 1290

| STIMULATOR | | GM-CSF (pg/ml) TIL[a] | |
|---|---|---|---|
| Cell line | Transfected genes | 1290 | 888 |

[c]Positive controls were carried out using TIL previously shown to recognize MART-1, gp100 and gp75. COS transfected with MART-1 plus HLA-A2, HLA-A2 alone or MART-1 alone stimulated the release of 1,800, 30 and <8 pg/ml of GM-CSF, respectively, from TIL 1235. COS transfected with gp100 plus HLA-A2, HLA-A2 alone or gp100 alone stimulated the release of 1,500, 50, and 40 pg/ml of GM-CSF, respectively, from TIL 1200. COS transfected with gp75 plus HLA-A31, HLA-A31 alone or gp75 alone stimulated the release of 770, 10 and 10 pg/ml of GM-CSF, respectively, from TIL 586.
[d]NEHN 2488 and NEHM 680 represent 2 normal human melanocyte lines.

TABLE 3

Comparison of TIL 1290 and TIL 888 Antigen Specificity

| STIMULATOR | | GM-CSF (PG/ML) TIL[a] | |
|---|---|---|---|
| Cell line | Tranfected gene | 1290 | 888 |
| 293-A24 | pCDNA3[b] | <10 | 60 |
| 293-A24 | tyrosinase | <10 | 750 |
| 293-A24 | p15 | 400 | 60 |
| 888 mel | None | 1,100 | 5,000 |
| 1290 mel | None | 660 | 2,300 |
| 624 mel | None | <10 | <10 |
| None | None | <10 | 30 |

[a]Assays were carried out with 2 × 10⁵ TIL as described in Materials and Methods in Example 1.
[b]293-A24 cells (10⁵) were transfected with 200 ng of plasmid containing the indicated genes overnight before incubation with TIL.

TABLE 4

Stimulation of Cytokine Release from TIL 1290 by Full Length and Truncated p15

| STIMULATOR | | GM-CSF (pg/ml) | |
|---|---|---|---|
| Cell line | Transfected gene[a] | Expt. 1 | Expt. 2 |
| COS-7 | p15 | 30 | 60 |
| COS-7 | HLA-A24 | 30 | 100 |
| COS-7 | p15 + HLA-A24 | 770 | 1,200 |
| COS-7 | Clone1[b] + HLA-A24 | 740 | 690 |
| COS-7 | Clone2 + HLA-A24 | 300 | 650 |
| COS-7 | β-gal + HLA-A24 | 40 | 150 |
| 888 | None | 3,200 | 1,100 |
| None | None | <10 | 30 |

[a]The indicated genes were transfected either alone or with a plasmid containing the HLA-A24 gene into 5 × 10⁴ cos cells.
[b]AN RT-PCR was carried out using RNA obtained from 888 EBV B cells with primers M2a and M2b as described in Materials and Methods in Example 1. The PCR products were cloned in pCDNA3 and tested along with the full length p15 gene for their ability to stimulate cytokine release from TIL 1290 following transfection into cos cells along with HLA-A24.

TABLE 5

Titration of p15 Peptides for Stimulation of TIL 1290

| PEPTIDE[a] | ug/ml | GM-CSF (pg/ml) |
|---|---|---|
| p15$_{10-18}$ | 10 | 910 |
| " | 1 | 600 |
| " | 0.1 | 390 |
| " | 0.01 | 80 |

TABLE 5-continued

Titration of p15 Peptides for Stimulation of TIL 1290

| PEPTIDE[a] | ug/ml | GM-CSF (pg/ml) |
|---|---|---|
| " | 0.001 | 20 |
| $p15_{9-18}$ | 10 | 780 |
| " | 1 | 570 |
| " | 0.1 | 390 |
| " | 0.01 | 70 |
| " | 0.001 | <10 |
| None | | 20 |
| 888 mel | | 2,000 |
| TIL alone | | 10 |

[a]Peptides were incubated with $10^5$ 888 EBV B cells at the indicated concentrations for 2 hours at 37°. Following this incubation, $10^5$ TIL 1290 were added, and 18 hours later supernatants harvested and assayed for GM-CSF using a GM-CSF Elisa Kit (R&D Company, Minneapolis, Minnesota).

EXAMPLE 2

Identification Of A Tyrosinase Epitope Recognized By HLA-A24 Restricted Tumor Infiltrating Lymphocytes (TIL)

Materials and Methods

Cell Lines

TIL 1413 cell line was generated by culturing lymphocytes obtained from tumor biopsy in AIM-V medium (Life Technologies, Inc., Gaithersburg, Md.) containing 5% human AB serum and 6000 international units/ml of interleukin 2 (IL-2) (Cetus-Oncogen Division, Chiron Corp., Emeryville, Calif.) for 30–70 days as previously described (Rosenberg, S. A., et al., Preliminary report. *New Engl. J. Med.*, (1988) 319: 1676–1680.

Melanoma cell lines (888 mel, 938 mel, 397 mel, and 586 mel) and Epstein-Barr virus transformed B cell lines (888 EBVB) were established in our laboratory and cultured in RPMI 1640 medium containing 10% fetal calf serum (FCS) (Topalian, S. L. et al., *J. Immunol.* 144:4487–4495). The monkey kidney cell line COS-7 was obtained from W. Leonard, NIH.

Exonuclease III deletion of the Tyrosinase Gene

Tyrosinase cDNA was cloned into the BstX I site of pcDNA3 (Robbins, P. F., et al., (1994) *Cancer Res.*, 54: 3124–3126; FIGS. 7A–7D). The plasmid was digested with Not I and Xba I. After incorporation of α-phosphoroth-ioate deoxynucleoside triphosphates into the Xba I site, a standard exonuclease III (Exo III) nested deletion was performed using Exo-Size Deletion Kit (New England Biolabs, Inc., Beverly, Mass.). The truncated DNA fragments were ligated, transformed into *E.coli* (DH5a, Life Technologies, Inc., Gaithersburg, Md.), and the plasmids containing cDNA fragments were purified. The nucleotide sequence of the various cDNA clones was determined using UBS sequence kit (Amersham, Cleveland, Ohio).

Identification of cDNA fragments containing epitope recognized by TIL 1413

COS-7 cells were transfected with the plasmids containing the truncated tyrosinase cDNA and HLA-A24 cDNA by Lipofectamine methods as previously described (Robbins, P. F., et al., (1994) *Cancer Res.*, 54: 3124–3126). Briefly, $1 \times 10^5$ COS-7 cells were plated in a flat-bottom 96-well microplate in Dulbecco's Modified Eagle's medium (DMEM) (Biofluids, Gaithersberg, Md.) without serum. 200 ng of plasmids containing the truncated genes was then mixed with 2 mg of Lipofectamine in 100 ml of DMEM for 15–45 min, added to COS cells, and incubated for 16 h. The following day, the transfection medium was removed, cells were rinsed twice with DMEM, and $1 \times 10^5$ TIL was added into each well in AIM-V medium containing 60 international units/ml of IL-2. After incubation for 18 hours (H), 100 ml of supernatant was collected and assayed for GM-CSF production using a granulocyte-macrophage colony stimulating factor (GM-CSF) ELISA kit (R+D Systems, Minneapolis, Minn.).

Peptide Synthesis and Identification of Antigenic Peptides

Peptides were synthesized by a solid phase method using a multiple synthesizer (Model AMS 422, Gilson co. Inc., Worthington, Ohio). The peptides were purified by HPLC on an R2 reverse phase column (Perseptive Biosystems, Cambridge, Mass.) with an acetonitrile gradient in 0.05% TFA/water. The identity of these peptides were confirmed by mass spectrometry. Epitope was identified by reactivity of T-cells against 888 EBVB cells preincubated with each peptide using GM-CSF release assay as described above and cytotoxicity assay as described in Kawakami, Y., et al., (1988) *J. Exp. Med.*, 168: 2183–2191.

The TIL 1413 line isolated from HLA-A24+ patient 1413 released GM-CSF when incubated with HLA-A24– melanoma cell lines, but not HLA-A24+ melanoma cell lines or the HLA-A24+ 888 EBVB line (Table 6). In addition, TIL 1413 also weakly lysed HLA-A24+ allogenic melanoma cell line (Table 7). These studies suggested that a shared melanoma antigen could be recognized by TIL 1413 in the context of HLA-A24.

Tyrosinase, a shared melanoma antigen, has previously been shown to be recognized by T cells in the context of two different class I HLA alleles, HLA-A2 and HLA-A24 (Brichard, V., et al., (1993) *J. Exo. Med.*, 178: 489–495; Robbins, P. F., et al., (1994) *Cancer Res.*, 54: 3124–3126). Whether TIL 1413 could recognize the tyrosinase antigen presented by HLA-A24 was tested. The COS cells transfected with both tyrosinase and HLA-A24 cDNA clearly stimulated GM-CSF release from TIL 1413. Neither tyrosinase nor HLA-A24 transfectants alone could stimulate this response (Table 6). Thus TIL 1413 appeared to recognize tyrosinase in an HLA-A24 restricted fashion.

Figure 5:
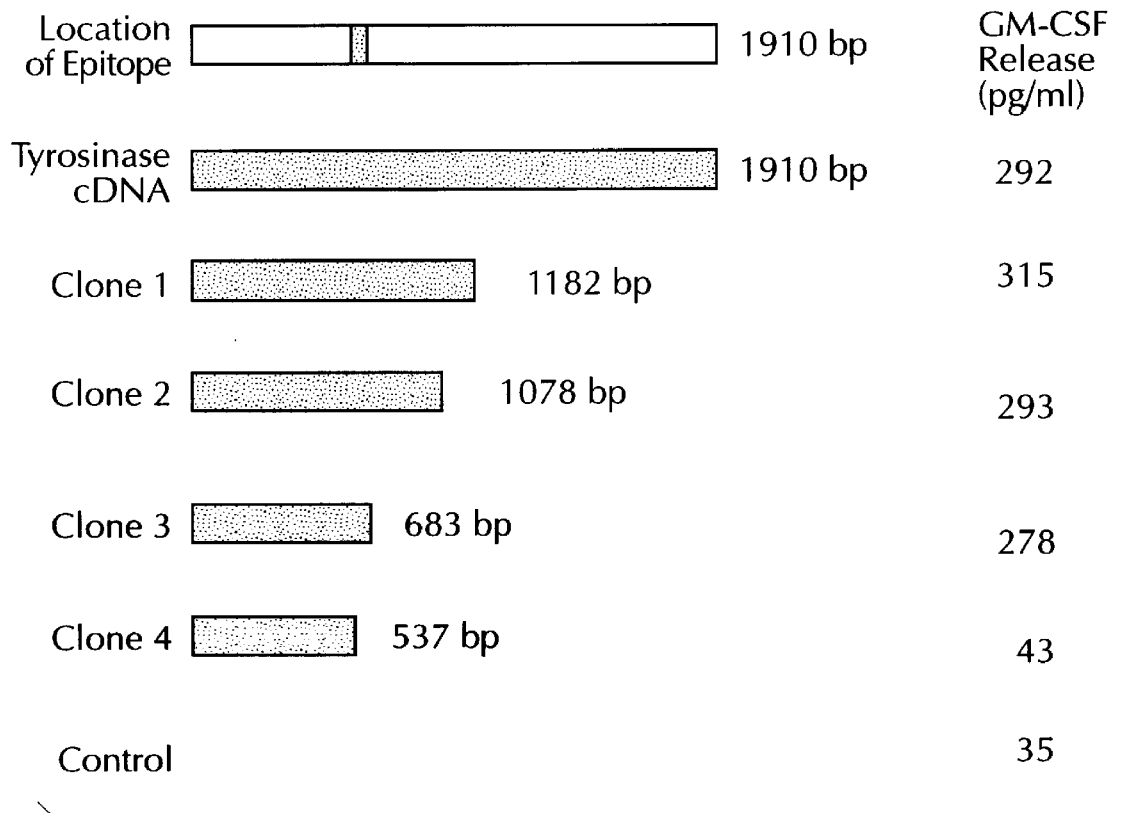
FIG. 5 shows the location of the tyrosinase epitope region recognized by TIL 1413. The full length clone and various truncated clones are shown in black boxes. Nucleotides are numbered from the start codon. The full length gene and the truncated clone were then transfected into COS-7 cells alone with HLA-A24 genes. The amount of granulocyte-macrophage colony stimulating factor (GM-CSF) released by TIL-1413 when incubated with these COS transfectants is shown at the right.

To identify the epitope recognized by TIL 1413, multiple truncated tyrosinase cDNA clones were using an exonuclease III deletion method. Exonuclease III generated removed nucleotides in the 3' to 5' direction at the Not I site and then created unidirectional nested deletions from the 3' end of tyrosinase cDNA. After ligation and isolation, these truncated tyrosinase cDNAs were then transfected into COS-7 cells along with the HLA-A24 cDNA to determine the region encoding epitope by testing TIL reactivity to the transfected COS cells using GM-CSF release assay. By determining the sequence of the truncated cDNA clones, the region coding for the epitope was delineated between 537 bp and 683 bp of the tyrosinase cDNA gene (FIG. 5).

Eleven peptides within this region were synthesized based on the suggested peptide binding motifs to HLA-A24 (Kubo, R. T., et al., (1994) *J. Immunol.*, 152: 3913–3924). The epitopes were screened by testing their ability to sensitize HLA-A24+ 888 EBVB cells to TIL lysis and their ability to render 888 EBVB cells to stimulate GM-CSF release from TIL (Table 7). TIL 1413 lysed 888 EBVB cells pulsed with either peptide T9206 or T10206 but not other peptides and also released GM-CSF when incubated with 888 EBVB cells pulsed with these two peptides. The peptides T9206 and T10206 are overlapping peptides; T10206 contains an additional leucine residue at the COOH-terminus.

Figure 6:
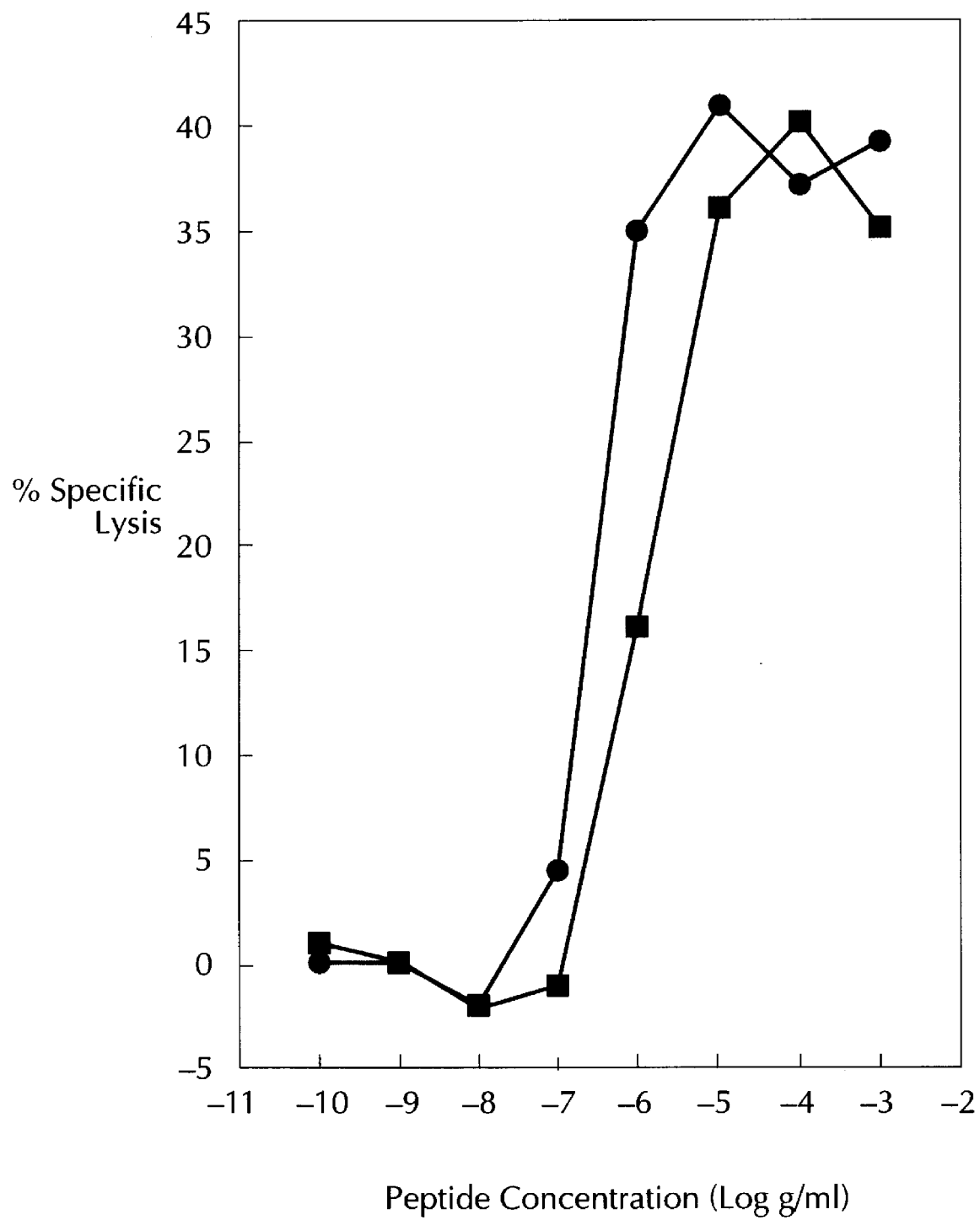
FIG. 6 shows titration analysis of tyrosinase peptides for recognition by TIL 1413. 888 EBVB target cells were labeled with $^{51}$Cr overnight, and then incubated with various concentration of the purified peptides T9206 and T10206 for 2 hours (h) respectively. Lysis of target cells by TIL 1413 were measured as $^{51}$Cr release after 4 h incubation at an effector : target ratio of 40:1 (T9206 -•-, T10206 -■-

The peptides T9206 (AFLPWHRLF; SEQ ID NO:7) and T10206 (AFLPWHRLFL; SEQ ID NO:8) were further purified and titrated in order to evaluate their relative ability to sensitize 888 EBVB cells to TIL lysis. Both peptides have a similar activity in sensitizing target cells, the maximal lysis of 888 EBVB cells pulsed with these peptides was about 40% (FIG. 6).

Tyrosinase, a enzyme involved in melanin synthesis, was recognized by T-cells in association with two different HLA restriction elements, HLA-A2 and HLA-A24 (Brichard, V., et al., (1993); *J. Exp. Med.*, 178: 489–495; Robbins, P. F., et al., (1994); *Cancer Res.*, 54: 3124–3126. Although two tyrosinase epitopes recognized by HLA-A2 restricted CTL have been previously described (Wolfel, T., et al., (1994); Eur. *J. Immunol.*, 24:759–764), the epitope of tyrosinase presented in the context of HLA-A24 has not been identified.

It was demonstrated that tyrosinase can be recognized by HLA-A24 restricted TIL from patient 1413 and have also identified a tyrosinase epitope recognized by TIL 1413. Tyrosinase has previously been shown to be recognized by T-cells from a patient with melanoma in association with two different HLA restriction elements, HLA-A2 and HLA-A24 (Brichard, V., et al., *J. Exp. Med.*, 178: 489–495, (1993); Robbins, P. F., et al., *Cancer Res.*, 54: 3124–3126, (1994)). Adoptive transfer of TIL 888, another HLA-A24 restricted tyrosinase specific TIL, resulted in complete cancer regression (Robbins, P. F., et al. (1994), *Cancer Res.*, 54: 3124–3126, suggesting that tyrosinase may represent an important tumor rejection antigen.

The use of COS cells transfected with a series of truncated cDNA generated by the exonuclease III gene deletion method was used to locate region containing an immunogenic epitope of tyrosinase. In order to create unidirectional deletions, the vector was cut with Xba I and filled with α-phosphorothioate deoxynucleotides which protect the plasmid from digestion with exonuclease III. The vector was also digested with Not I, which served as the starting point for digestion. Since the deletion can be controlled by varying the time of digestion, various sizes of the truncated gene can be generated by this method and the region containing the epitopes can be narrowed.

Based on titration analysis, T9206 (SEQ ID NO:7) and T10206 (SEQ ID NO:8) peptides sensitized target cells to lysis with similar efficiency (FIG. 6). The 9-mer peptide, T9206, probably represents the naturally processed peptide on tumor cell surface, since the predominant size of peptides eluted from class I MHC molecules has been reported to be nine amino acids (Hunt, D. F., et al., (1992) *Science* (Washington, D.C.), 255: 1261–1263). A CTL line generated using T9206 peptide from the PBL of patient 1413 was also found to lyse HLA-A24+ melanoma cells suggesting that this peptide may be processed and presented on the surface of melanoma cells. This also provides further evidence that the same cells in the polyclonal TIL population which recognized T9206 are capable of lysing melanoma cells.

All melanoma antigens identified so far, including MAGE-1, MAGE-3, gp100, MART-1, and tyrosinase, are non-mutated self-antigens (Van der Bruggen, P., et al. (1991), *Science* (Washington D.C.), 254: 1643–1647; Gaugler, B., et al. (1994), *J. Exp. Med.*, 197: 921–930; Kawakami, Y. et al., (1994), *Proc. Natl. Acad. Sci. (USA.)*, 91:6458–6462; Bakker, A. B. H., et al. (1994), *J. Exy. Med.*, 179: 1005–1009; Kawakami, Y., et al., *Proc. Natl. Acad. Sci. (USA)*, 91: 3515–3519; Brichard, V., et al., *J. Exo. Med.* (1993), 178: 489–495; Robbins, P. F., et al., *Cancer Res.*, (1994) 54: 3124–3126, (1994). The identification of genes and immunogenic peptides associated with melanoma tumor antigens opens new possibilities for active specific immunization approaches to the immunotherapy of patients with cancer.

TABLE 6

Specific secretion of GM-CSF by TIL 1413

| Cell | Stimulator Transfected gene | HLA-A24 expression | GM-CSF Secretion (pg/ml)[a] |
|---|---|---|---|
| 888 Mel[b] | none | + | 865 |
| 938 Mel | none | + | 538 |
| 586 Mel | none | − | 56 |
| 397 Mel | none | − | 31 |
| 888 EBVB | none | + | 28 |
| COS-7[c] | none | − | 35 |
| COS-7 | HLA-A24 | + | 31 |
| COS-7 | tyrosinase | − | 38 |
| COS-7 | tyrosinase + HLA-A24 | + | 292 |
| COS-7 | β-gal + HLA-A24 | + | 30 |

[a]TIL in the absence of melanomas secreted <40 pg/ml GM-CSF.
[b]5 × 10⁵/ml melanoma cells were incubated with TIL.
[c]COS-7 cells were transfected as described in Example 2.

TABLE 7

TIL 1413 recognition of melanoma cells and EBVB 888 cells preincubated with synthetic tyrosinase peptides

| Cell | Target Peptide | HLA-A24 | % Specific Lysis[a] | GM-CSF (pg/ml) |
|---|---|---|---|---|
| 888 Mel | none | + | 12 | >1,000 |
| 938 Mel | none | + | 8 | ND[b] |
| 586 Mel | none | − | −1 | ND |
| 397 Mel | none | − | 0 | ND |
| 888 EBVB[c] | none | + | 0 | 89 |
| 888 EBVB | T10166 (MFNDINIYDL) (SEQ ID NO:9) | + | −1 | 93 |
| 888 EBVB | T9177 (VWMHYYVSM) (SEQ ID NO:10) | + | 0 | 93 |
| 888 EBVB | T9180 (HYYVSMDAL) (SEQ ID NO:11) | + | 2 | 117 |
| 888 EBVB | T10180 (HYYVSMDALL) (SEQ ID NO:12) | + | 1 | 79 |
| 888 EBVB | T9181 (YYVSMDALL) (SEQ ID NO:13) | + | −1 | 144 |
| 888 EBVB | T9199 (DFAHEAPAF) (SEQ ID NO:14) | + | 0 | 133 |
| 888 EBVB | T10199 (DFAHEAPAFL) (SEQ ID NO:15) | + | 1 | 101 |
| 888 EBVB | T9206 (AFLPWHRLF) (SEQ ID NO:7) | + | 26 | >1,000 |

TABLE 7-continued

TIL 1413 recognition of melanoma cells and EBVB 888 cells preincubated with synthetic tyrosinase peptides

| Cell | Target Peptide | HLA-A24 | % Specific Lysis[a] | GM-CSF (pg/ml) |
|---|---|---|---|---|
| 888 EBVB | T10206 (AFLPWHRLFL) (SEQ ID NO:8) | + | 20 | >1,000 |
| 888 EBVB | T10209 (PWHRLFLLRW) (SEQ ID NO:16) | + | 0 | 153 |
| 888 EBVB | T10213 (LFLLRWEQEI) (SEQ ID NO:17) | + | 1 | 81 |

[a]% of lysis by TIL 1413 was shown at effector (E): target (T) ratio of 40:1.
[b]Not determined in this experiment.
[c]EBVB, Epstein-Barr virus-transformed cells. 888 EBVB was typed as HLA-A1 and HLA-A24.

EXAMPLE 4

P-15 Vaccines As A Treatment For Melanoma In Mammals

P-15 vaccines may be efficacious in treating mammals afflicted with melanoma. For example, p15 vaccines may be administered to individuals. Mammals can be immunized with the recombinant proteins described herein in ranges of 1 mg–100 mg. Alternatively mammals, preferably humans may be immunized with the p15 nucleic acid sequence inserted into a viral vector such as vaccinia virus, adenovirus or fowl pox virus. By way of example, the nucleic acid sequences encoding the p15 immunogenic peptides AYGLDFYIL ($p15_{10-18}$; SEQ ID NO:5) and EAYGLDFYIL ($p15_{9-18}$; SEQ ID NO:6) can be used. A range of about $10^6$–$10^{11}$ viral particles carrying the p15 nucleic acid sequences can be administered per mammal, preferably a human. The mammals will be monitored for antibodies to the immunogen or increase in cytotoxic lymphocytes (CTL) recognizing the immunogen by conventional methods or alleviation of clinical signs and symptoms of the active disease. Specific parameters to be assessed include production of immune cells that recognize the vaccine antigen or tumor regression. Such vaccines may be administered either prophylactically or therapeutically. Mammals may also be immunized with the p15 nucleic acid sequence inserted into a retroviral vector. Suggested dose ranges of the antigen in retroviruses are $10^6$–$10^{11}$ viral particles per mammal, preferably a human. Response and efficacy of the retroviral vaccines will be assessed as described above. Alternatively, the nucleic acids corresponding to the HLA-A24 immunogenic tyrosinase peptides AFLPWHRLF (SEQ ID NO:7) and AFLPWHRLFL (SEQ ID NO:8) may be inserted into vectors and used as vaccines.

EXAMPLE 5

Use Of Lymphocytes Sensitized To Immunogenic Peptides Derived From Melanoma Antigens For Therapeutically Treating Mammals Afflicted With Melanoma T-lymphocytes presensitized to the melanoma antigen may be effective in therapeutically treating mammals afflicted with melanoma. The T-lymphocytes are isolated from peripheral blood lymphocytes or tumor infiltrating lymphocytes and exposed in vitro to the p15 protein or peptide. T-lymphocytes are isolated from peripheral blood or melanoma tumor suspensions and cultured in vitro (Kawakami, Y. et al. (1988) *J. Exp. Med.* 168: 2183–2191). Examples of peptides include, but are not limited to, AYGLDFYIL ($p15_{10-18}$; SEQ ID NO:5), EAYGLDFYIL ($p15_{9-18}$; SEQ ID NO:6), AFLPWHRLF (SEQ ID NO:7) and AFLPWHRLFL (SEQ ID NO:8). Peptide-specific cells can be generated essentially as previously described (Cellis et al. (1994) *Proc. Natl. Acad. Sci. USA* 91:2105–2109). Briefly, antigen presenting cells expressing the appropriate MHC class I allele may be exposed to p15 or tyrosinase peptides at a concentration of about 1 to 10 μg/ml for a period of 1–16 hours. Antigen presenting cells include but are not limited to peripheral blood mononuclear cells, EBVB cells, purified monocytes, macrophages, and dendritic cells. T cells can then be incubated with peptide-pulsed antigen presenting cells for a period of about 7 to 10 days, and repeatedly stimulated in the same manner about 3 to 10 times. T-lymphocytes exposed to the antigen will be administered to the mammal, preferably a human at about $10^9$–$10^{12}$ lymphocytes per mammal. The lymphocytes may be administered either intravenously, intraperitoneally or intralesionally. This treatment may be administered concurrently with other therapeutic treatments such as cytokines, radiotherapy, surgical excision of melanoma lesions and chemotherapeutic drugs, adoptive T lymphocyte therapy.

The present invention is not to be limited in scope by the nucleic acid sequences disclosed or deposited, since the deposited embodiment is intended as a single illustration of one aspect of the invention and any sequences which are functionally equivalent are within the scope of this invention. Indeed, various modifications of the invention in addition to those shown and described herein will become apparent to those skilled in the art from the foregoing description and accompanying drawings. Such modifications are intended to fall within the scope of the claims appended hereto.

We claim:

1. An isolated nucleic acid sequence encoding p15 (SEQ ID NO:2.

2. An isolated nucleic acid sequence having the sequence shown in FIG. 1 (SEQ ID NO:1).

3. An isolated nucleic acid sequence wherein said sequence is an allelic variant of the sequence shown in FIG. 1 (SEQ ID NO:1).

4. An isolated nucleic acid sequence wherein said sequence is variant of the sequence in FIG. 1 (SEQ ID NO:1).

5. An isolated nuleic acid sequence, wherein said sequence is a complement of a sequence capable of specifically hybridizing to a nucleic acid sequence shown in FIG. 1.

6. A method of producing recombinant p15 protein comprising, culturing a host cell transformed with a vector comprising the nucleic acid sequence shown in FIG. 1 under conditions to cause expression of the protein.

7. The method of claim 6, wherein the expression vector is a eukaryotic expression vector.

8. The method of claim 6, wherein the expression vector is a baculovirus vector.

9. The method of claim 6, wherein the host cell is a eukaryotic cell.

10. The method of claim 9, wherein the eukaryotic cell is an insect cell.

11. A recombinant expression vector comprising the nucleic acid sequence of claims 1,2,3,4, or 5 or a fragment thereof which specifically hybridizes with nucleic acids encoding p15.

12. A host cell transformed or transfected with the recombinant expression vector of claim 11.

13. A purified and isolated nucleic acid sequence encoding a peptide comprising at least about 8 contiguous amino acids of the p15 sequence as shown in FIG. 1 (SEQ ID NO:2) or an allelic variant thereof, said peptide being specifically recognized by tumor infiltrating lymphocytes (TIL).

14. A recombinant expression vector comprising the nucleic acid sequence of claim 13.

* * * * *